(12) United States Patent
Farritor et al.

(10) Patent No.: US 9,579,088 B2
(45) Date of Patent: Feb. 28, 2017

(54) METHODS, SYSTEMS, AND DEVICES FOR SURGICAL VISUALIZATION AND DEVICE MANIPULATION

(75) Inventors: Shane M. Farritor, Lincoln, NE (US);
Mark Rentschler, Omaha, NE (US);
Amy Lehman, Seward, NE (US);
Nathan A. Wood, Papillion, NE (US);
Adam Bock, Sun Prairie, WI (US);
Reed Prior, Waltham, MA (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 1159 days.

(21) Appl. No.: 11/966,741

(22) Filed: Dec. 28, 2007

(65) Prior Publication Data

US 2008/0221591 A1 Sep. 11, 2008

Related U.S. Application Data

(60) Provisional application No. 60/890,691, filed on Feb. 20, 2007, provisional application No. 60/956,032, (Continued)

(51) Int. Cl.
*A61B 1/00* (2006.01)
*A61B 17/00* (2006.01)
(Continued)

(52) U.S. Cl.
CPC ........ *A61B 17/00234* (2013.01); *A61B 34/70* (2016.02); *A61B 34/74* (2016.02);
(Continued)

(58) Field of Classification Search
CPC .......... A61B 17/00234; A61B 1/00105; A61B 1/041; A61B 34/70; A61B 34/74; A61B 90/36
(Continued)

(56) References Cited

U.S. PATENT DOCUMENTS 3,870,264 A  3/1975 Robinson
3,989,952 A  11/1976 Hohmann
(Continued)

FOREIGN PATENT DOCUMENTS

CN  1082821918  12/2012
EP  1354670  10/2003
(Continued)

OTHER PUBLICATIONS

International Search Report and Written Opinion issued in PCT/US2008/069822, mailed Aug. 5, 2009, 10 pages.
(Continued)

*Primary Examiner* — Timothy J Neal
(74) *Attorney, Agent, or Firm* — Davis, Brown, Koehn, Shors & Roberts, P.C.; Sean D. Solberg

(57) ABSTRACT

A surgical device includes a console having a visual display and a manipulator arm, a robotic device having a camera and a connection component. The robotic device is configured to be positioned completely within a body cavity. The camera is configured to transmit visual images to the visual display. The connection component operably couples the console and the robotic device. The manipulator arm is positioned relative to the visual display so as to appear to be penetrating the visual display.

20 Claims, 18 Drawing Sheets

Related U.S. Application Data filed on Aug. 15, 2007, provisional application No. 60/983,445, filed on Oct. 29, 2007.

(51) Int. Cl.
    A61B 1/04      (2006.01)
    A61B 1/06      (2006.01)
    A61B 1/313     (2006.01)
    A61B 17/29     (2006.01)

(52) U.S. Cl.
    CPC ............... *A61B 90/36* (2016.02); *A61B 1/06* (2013.01); *A61B 1/3132* (2013.01); *A61B 17/29* (2013.01); *A61B 34/30* (2016.02); *A61B 90/37* (2016.02); *A61B 2017/2919* (2013.01); *A61B 2034/302* (2016.02); *A61B 2034/742* (2016.02); *A61B 2090/372* (2016.02); *A61B 2090/373* (2016.02)

(58) Field of Classification Search
    USPC ........ 600/103, 104, 106, 109, 110, 112, 113, 600/114, 118, 160, 101–102; 434/262; 385/65; 700/249, 259, 262; 606/1, 130
    See application file for complete search history.

(56) References Cited

U.S. PATENT DOCUMENTS

| | | |
|---|---|---|
| 4,246,661 A | 1/1981 | Pinson |
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyake |
| 4,623,183 A | 11/1986 | Amori |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,897,014 A | 1/1990 | Tietze |
| 4,922,755 A | 5/1990 | Oshiro et al. |
| 4,990,050 A | 2/1991 | Tsuge et al. |
| 5,019,968 A | 5/1991 | Wang et al. |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,259,365 A * | 11/1993 | Nishikori et al. ............ 600/102 |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,388,528 A | 2/1995 | Pelrine et al. |
| 5,436,542 A | 7/1995 | Petelin et al. |
| 5,441,494 A | 8/1995 | Ortiz |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rostoker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,873,814 A * | 2/1999 | Adair ............................ 600/109 |
| 5,876,325 A * | 3/1999 | Mizuno .............. A61B 1/00048 600/102 |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,367 A * | 10/2000 | Adair ............................ 600/101 |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |

(56) References Cited

U.S. PATENT DOCUMENTS

| | | |
|---|---|---|
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Okamoto et al. |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 * | 10/2002 | Ohtsuki ............... 700/247 |
| 6,491,691 B1 | 12/2002 | Morley et al. |
| 6,491,701 B2 | 12/2002 | Tierney et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,569,084 B1 * | 5/2003 | Mizuno et al. ............. 600/102 |
| 6,574,355 B2 * | 6/2003 | Green ..................... 382/128 |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 * | 5/2004 | Green ........................... 700/3 |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 * | 12/2004 | Wang et al. ................. 700/258 |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 * | 10/2005 | Ghodoussi et al. ......... 600/101 |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |

(56) References Cited

U.S. PATENT DOCUMENTS

| | | |
|---|---|---|
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2* | 1/2011 | Moll et al. .................... 700/245 |
| 7,960,935 B2 | 6/2011 | Farritor et al. |
| 8,021,358 B2 | 9/2011 | Doyle et al. |
| 8,179,073 B2 | 5/2012 | Farritor et al. |
| 8,353,897 B2 | 1/2013 | Doyle et al. |
| 9,089,353 B2 | 7/2015 | Farritor |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszka et al. |
| 2002/0038077 A1 | 3/2002 | de la Torre et al. |
| 2002/0065507 A1 | 5/2002 | Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julien et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1* | 6/2003 | Cadeddu et al. ............. 600/114 |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth et al. |
| 2004/0138525 A1 | 7/2004 | Saadat |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0242968 A1* | 12/2004 | Hill et al. .................... 600/102 |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1* | 2/2005 | Oleynikov et al. ...... 318/568.12 |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0096502 A1* | 5/2005 | Khalili ........................ 600/106 |
| 2005/0143644 A1 | 6/2005 | Gilad et al. |
| 2005/0154376 A1* | 7/2005 | Riviere et al. .................... 606/1 |
| 2005/0165449 A1* | 7/2005 | Cadeddu et al. ............. 606/232 |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1* | 7/2006 | Lipow ............................. 606/1 |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake |
| 2007/0032701 A1 | 2/2007 | Fowler et al. |
| 2007/0038020 A1* | 2/2007 | Tien ............................. 600/102 |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0129604 A1* | 6/2007 | Hatcher et al. ............... 600/136 |
| 2007/0142725 A1 | 6/2007 | Hardin et al. |
| 2007/0156019 A1 | 7/2007 | Larkin et al. |
| 2007/0156157 A1* | 7/2007 | Nahum et al. ............... 606/130 |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Okeynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1* | 2/2008 | Williams ............ A61B 1/00052 600/204 |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0111513 A1 | 5/2008 | Farritor et al. |
| 2008/0119870 A1 | 5/2008 | Williams |
| 2008/0132890 A1 | 6/2008 | Woloszko et al. |
| 2008/0161804 A1 | 7/2008 | Rioux et al. |
| 2008/0164079 A1 | 7/2008 | Jacobsen |

(56) References Cited

U.S. PATENT DOCUMENTS

| | | |
|---|---|---|
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1* | 12/2009 | Guru et al. .......... 434/262 |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Scott |
| 2010/0204713 A1 | 8/2010 | Ruiz |
| 2010/0245549 A1 | 9/2010 | Allen et al. |
| 2010/0262162 A1 | 10/2010 | Omori |
| 2010/0292691 A1 | 11/2010 | Brogna |
| 2010/0318510 A1 | 12/2010 | Farritor et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0077478 A1 | 3/2011 | Freeman et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0264078 A1 | 10/2011 | Lipow |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0116362 A1 | 5/2012 | Kieturakis |
| 2012/0179168 A1 | 7/2012 | Farritor |
| 2012/0253515 A1 | 10/2012 | Coste-Maniere et al. |
| 2013/0041360 A1 | 2/2013 | Farritor |
| 2013/0131695 A1 | 5/2013 | Scarfogliero et al. |
| 2014/0039515 A1 | 2/2014 | Mondry et al. |
| 2014/0046340 A1 | 2/2014 | Wilson et al. |
| 2014/0303434 A1 | 10/2014 | Farritor et al. |

FOREIGN PATENT DOCUMENTS

| | | |
|---|---|---|
| EP | 2286756 | 2/2011 |
| EP | 2286756 A1 | 2/2011 |
| EP | 2329787 | 8/2011 |
| JP | 2004144533 | 5/1990 |
| JP | 5115425 | 5/1993 |
| JP | 200716235 | 6/1993 |
| JP | 2006507809 | 9/1994 |
| JP | 07 136173 | 5/1995 |
| JP | 07306155 | 11/1995 |
| JP | 7306155 | 11/1995 |
| JP | 08-224248 | 9/1996 |
| JP | 2001500510 | 1/2001 |
| JP | 2001505810 | 5/2001 |
| JP | 2003220065 | 8/2003 |
| JP | 2004322310 | 6/2004 |
| JP | 2004180781 | 7/2004 |
| JP | 2004-322310 A | 11/2004 |
| JP | 2004329292 | 11/2004 |
| JP | 2006508049 | 3/2006 |
| JP | 2009-106606 | 5/2009 |
| JP | 2010-533045 | 10/2010 |
| JP | 2010-536436 | 12/2010 |
| JP | 2011-504794 | 2/2011 |
| JP | 2011-045500 | 3/2011 |
| JP | 2011-115591 | 6/2011 |
| WO | WO 92/21291 | 12/1992 |
| WO | WO 02/082979 | 10/2002 |
| WO | 02100256 | 12/2002 |
| WO | WO 02/100256 | 12/2002 |
| WO | WO 2005/009211 | 2/2005 |
| WO | WO 2005044095 | 5/2005 |
| WO | WO 2006 005075 | 1/2006 |
| WO | WO 2006/079108 | 1/2006 |
| WO | WO 2006/052927 | 5/2006 |
| WO | WO2006079108 | 7/2006 |
| WO | WO 2007011654 | 1/2007 |
| WO | WO 2007/111571 | 10/2007 |
| WO | WO 2007/149559 | 12/2007 |
| WO | WO 2009023851 A1 | 2/2009 |
| WO | WO 2009/144729 | 12/2009 |
| WO | WO2010/042611 | 4/2010 |
| WO | WO2010/046823 | 4/2010 |
| WO | WO2010050771 A2 | 5/2010 |
| WO | WO 2011/118646 A1 | 9/2011 |
| WO | WO 2011/135503 A1 | 11/2011 |
| WO | WO 2011075693 | 7/2012 |
| WO | WO 2013009887 | 1/2013 |

OTHER PUBLICATIONS

Fraulob et al., "Miniature assistance module for robot-assisted heart surgery," *Biomed. Tech.* 2002, 47 Suppl. 1, Pt. 1, 4 pp.

Guber et al., "Miniaturized Instrument Systems for Minimally Invasive Diagnosis and Therapy," *Biomedizinische Technik*, 2002, Band 47, Erganmngsband 1: 198-201.

Thomann et al., "The Design of a new type of Micro Robot for the Intestinal Inspection," *Proceedings of the 2002 IEEE/RSJIntl. Conference on Intelligent Robots and Systems EPFL*, Oct. 2002, 1385-1390.

Guo et al., "Fish-like Underwater Microrobot with 3 DOF," *Proceedings of the 2002 IEEE International Conference on Robotics & Automation*, May 2002, 738-743.

Fukuda et al., "Mechanism and Swimming Experiment of Micro Mobile Robot in Water," *Proceedings of the 1994 IEEE International Conference on Robotics and Automation*, 1994, 814-819.

Guo et al., "Micro Active Guide Wire Catheter System—Characteristic Evaluation, Electrical Model and Operability Evalu-ation of Micro Active Catheter," *Proceedings of the 1996 IEEE International Conference on Robotics and Automation*, Apr. 1996, 2226-2231.

Yu et al., "Microrobotic Cell Injection," *Proceedings of the 2001 IEEE International Conference on Robotics & Automation*, May 2001, 620-625.

Ruurda et al., "Robot-assisted surgical systems: a new era in laparoscopic surgery," *Ann. R. Coll. Surg. Engl*, 2002, 84: 223-226.

Menciassi et al., "Robotic Solutions and Mechanisms for a Semi-Autonomous Endoscope," *Proceedings of the 2002 IEEE Intl. Conference on Intelligent Robots and Systems EPFL*, Oct. 2002, 1379-1384.

Ishiyama et al., "Spiral-type Micro-machine for Medical Applications," *2000 International Symposium on Micromechatronic and Human Science*, 2000, 65-69s.

Fearing et al., "Wing Transmission for a Micromechanical Flying Insect," *Proceedings of the 2000 IEEE International Conference on Robotics & Automation*, Apr. 2000, 1509-1516.

Mei et al., "Wireless Drive and Control of a Swimming Microrobot," *Proceedings of the 2002 IEEE International Conference on Robotics & Automation*. May 2002, 1131-1136.

(56) References Cited

OTHER PUBLICATIONS

Yu, "M2A™ Capsule Endoscopy A Break-through Diagnostic Tool for Small Intestine Imaging," *Gastroenterology Nursing*, 2001, 25(1): 24-27.

Miller et al., "In-Vivo Stereoscopic Imaging System with Five Degrees-of-Freedom for Minimal Access Surgery," Dept. of Computer Science and Dept. of Surgery, Columbia University, New York, NY, p. 7 , no date.

Strong et al., "Efficacy of Novel Robotic Camera vs. a Standard Laparoscopic Camera," *Surgical Innovation*, Westminster Publications, Inc., Dec. 2005, 12(4): 315-318.

Worn et al., "Esprit Project No. 33915: Miniaturized Robot for Micro Manipulation (Miniman)," Miniman Consortium, Mar. 22, 2002, 55 pp.

Meron, "The development of the swallowable video capsule (M2A)," *Gastrointestinal Endoscopy*, 2000, 52(6): 817-819.

Phee et al., "Development of Microrobotic Devices for Locomotion in the Human Gastrointestinal Tract," *International conference on Computational Intelligence*, no date.

Breda et al., "Future developments and perspectives in Lacroscopy," *Eur. Urology*, 2001, 40(1): 84-91.

Allendorf et al., "Postoperative Immune Function Varies Inversely with the Degree of Surgical Trauma in a Murine Model," *Surgical Endoscopy*, 1997, 11: 427-430.

Ang, "Active Tremor Compensation in Handheld Instrument for Microsurgery," *Doctoral dissertation, tech report CMU-RI-TR-04-28, Robotics Institute, Carnegie Mellon University*, May 2004, 150 pp.

Atmel 80C5X2 Core, http://www.atmel.com, 2006.

Bailey et al., "Complications of Laparoscopic Surgery," *Quality Medical Publishers, Inc.*, 1995, 25 pp.

Ballantyne, "Robotic Surgery, Telerobotic Surgery, Telepresence, and Telementoring," *Surgical Endoscopy*, 2002, 16: 1389-1402.

Begos et al., "Laparoscopic Cholecystectomy: From Gimmick to Gold Standard," *J Clin Gastroenterol*, 1994, 19(4): 325-330.

Calafiore et al., "Multiple Arterial Conduits Without Cardiopulmonary Bypass: Early Angiographic Results," *Ann Thorac Surg*, 1999, 67: 450-456.

Camarillo et al., "Robotic Technology in Surgery: Past, Present, and Future," *The American Journal of Surgery*, 2004, 188: 2S-15S.

Çavuş oğlu et al., "Robotics for Telesurgery: Second Generation Berkeley/UCSF Laparoscopic Telesurgical Workstation and Looking Towards the Future Applications," *Industrial Robot: An International Journal*, 2003, 30(1): 22-29.

Çavuş oğlu et al., "Telesurgery and Surgical Simulation: Haptic Interfaces to Real and Virtual Surgical Environments," Touch in virtual environments, IMSC Series in Multimedia, 2001, 28 pp.

Choi et al., "Flexure-based Manipulator for Active Handheld Microsurgical Instrument," *Proceedings of the 27th Annual International Conference of the IEEE Engineering in Medicine and Biology Society (EMBS)*, Sep. 2005.

CrystalEyes, http://www.reald.com, 2007 (Stereo3D visualization for CAVEs, theaters and immersive environments), 1pg.

Cuschieri, "Technology for Minimal Access Surgery," *BMJ*, 1999, 319:1-6.

Stefanini et al., "Modeling and Experiments on a Legged Microrobot Locomoting in a Tubular, Compliant and Slippery Environment," *Int. Journal of Robotics Research*, May-Jun. 2006, 25(5-6): 551-560.

Dumpert et al., "Improving In Vivo Robot Vision Quality," *Proceedings of Medicine Meets Virtual Reality*, Long Beach, CA, Jan. 26-29, 2005.

Faraz et al., "Engineering Approaches to Mechanical and Robotic Design for Minimally Invasive Surgery (MIS)," *Kluwer Academic Publishers* (Boston), 2000, 13 pp.

Flynn et al, "Tomorrow's Surgery; Micro-motors and Microrobots for Minimally Invasive Procedures," *Minimally Invasive Surgery & Allied Technologies*, 1998, 7(4): 343-52.

Franklin et al., "Prospective Comparison of Open vs. Laparoscopic Colon Surgery for Carcinoma: Five-Year Results," Dis Colon Rectum, 1996, 39: S35-S46.

Fukuda et al., "Micro Active Catheter System with Multi Degrees of Freedom," *Proceedings of the IEEE International Conference on Robotics and Automation*, May 1994, 2290-2295.

Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committee," *U.S. Food and Drug Administration*, available at http://www.fda.gov, Finalized: Nov. 7, 2003; Updated: Jun. 24, 2005, 11 pp.

Glukhovsky et al., "The development and application of wireless capsule endoscopy," Int. J. Med. Robot. Comput. Assist. Surgery, 2004, 1(1): 114-123.

Slatkin et al., "The Development of a Robotic Endoscope," *Proceedings of the 1995 IEEE International Conference on Robotics and Automation*, 1995, 162-171.

Hanly et al., "Value of the SAGES Learning Center in introducing new technology," *Surgical Endoscopy*, 2004, 19(4): 477-483.

Hanly et al., "Robotic Abdominal Surgery," *The American Journal of Surgery*, 2004; 188 (Suppl. to Oct. 1994): 19S-26S.

Heikkinen et al., "Comparison of laparoscopic and open Nissen fundoplication 2 Years after operation: A prospective randomized trial," *Surgical Endoscopy*, 2000, 14: 1019-1023.

Horgan et al., "Technical Report: Robots in Laparoscopic Surgery," *Journal of Laparoendoscopic & Advanced Surgical Techniques*, 2001, 11(6): 415-419.

Jagannath et al., "Peroral transgastric endoscopic ligation of fallopian tubes with long-term survival in a porcine model," *Gastrointestinal Endoscopy*, 2005, 61(3): 449-453.

Kalloo et al., "Flexible transgastric peritoneoscopy: a novel approach to diagnostic and therapeutic interventions in the peritoneal cavity," *Gastrointestinal Endoscopy*, 2004, 60(1): 114-117.

Kantsevoy et al., "Transgastric endoscopic splenectomy," *Surgical Endoscopy*, 2006, 20: 522-525.

Kantsevoy et al., "Endoscopic gastrojejunostomy with survival in a porcine model," *Gastrointestinal Endoscopy*, 2005, 62(2): 287-292.

Kim, "Early Experience with Telemanipulative Robot-Assisted Laparoscopic Cholecystectomy Using da Vinci," *Surgical Laparoscopy, Endoscopy & Percutaneous Techniques*, 2002, 12(1): 33-40.

Ko et al., "Per-Oral transgastric abdominal surgery," *Chinese Journal of Digestive Diseases*, 2006, 7: 67-70.

Lafullarde et al., "Laparoscopic Nissen Fundoplication: Five-year Results and Beyond," *Arch/Surg*, Feb. 2001, 136: 180-184.

Liem et al., "Comparison of Conventional Anterior Surgery and Laparoscopic Surgery for Inguinal-hemia Repair," *New England Journal of Medicine*, 1997, 336(22): 1541-1547.

MacFarlane et al., "Force-Feedback Grasper Helps Restore the Sense of Touch in Minimally Invasive Surgery," *Journal of Gastrointestinal Surgery*, 1999, 3: 278-285.

Mack, "Minimally Invasive and Robotic Surgery," *JAMA*, Feb. 2001, 285(5): 568-572.

Mack et al., "Present Role of Thoracoscopy in the Diagnosis and Treatment of Diseases of the Chest," *Ann Thorac Surgery*, 1992, 54: 403-409.

Menciassi et al., "Locomotion of a Legged Capsule in the Gastrointestinal Tract: Theoretical Study and Preliminary Technological Results," IEEE Int. Conf. on Engineering in Medicine and Biology, San Francisco, CA, Sep. 2004, 2767-2770.

Oleynikov et al., "Miniature Robots Can Assist in Laparoscopic Cholecystectomy," *Journal of Surgical Endoscopy*, 2005, 19(4): 473-476.

Hissink, "Olympus Medical develops capsule camera technology," Dec. 2004, accessed Aug. 29, 2007, http://www.letsgodigital.org , 3 pp.

Park et al., "Experimental studies of transgastric gallbladder surgery: cholecystectomy and cholecystogastric anastomosis (videos)," *Gastrointestinal Endoscopy*, 2005, 61(4): 601-606.

Patronik et al., "Preliminary evaluation of a mobile robotic device for navigation and intervention on the beating heart," *Computer Aided Surgery*, Jul. 2005, 10(4): 225-232.

(56) References Cited

OTHER PUBLICATIONS

Patronik et al., "Crawling on the Heart: A Mobile Robotic Device for Minimally Invasive Cardiac Interventions," *MICCAI*, 2004, 9-16.
Phee et al., "Analysis and Development of Locomotion Devices for the Gastrointestinal Tract," *IEEE Transaction on Biomedical Engineering*, Jun. 2002, 49(6): 613-616.
Rentschler et al., "An In Vivo Mobile Robot for Surgical Vision and Task Assistance," *ASME Journal of Medical Devices*, Mar. 2007, 1: 23-29.
Rentschler et al., "Mechanical Design of Robotic In Vivo Wheeled Mobility," *ASME Journal of Mechanical Design*, 2006a, 1-11.
Rentschler et al., "Mobile In Vivo Camera Robots Provide Sole Visual Feedback for Abdominal Exploration and Cholecystectomy," *Journal of Surgical Endoscopy*, 2006b, 20(1): 135-138.
Rentschler et al., "Modeling, Analysis, and Experimental Study of In Vivo Wheeled Robotic Mobility," *IEEE Transactions on Robotics*, 22(2): 308-321, 2006c.
Rentschler et al., "Natural Orifice Surgery with an Endoluminal Mobile Robot," *The Society of American Gastrointestinal Endoscopic Surgeons*, Dallas, TX, Apr. 2006d.
Rentschler et al., "Mobile In Vivo Biopsy and Camera Robot," *Studies in Health and Informatics—Medicine Meets Virtual Reality*, 2006e, 119: 449-454, IOS Press, Long Beach, CA.
Rentschler et al., "Toward In Vivo Mobility," *Studies in Health Technology and Informatics—Medicine Meets Virtual Reality*, ISO Press, Long Beach, CA, 2005a, 111: 397-403.
Rentschler et al., "Mobile In Vivo Robots Can Assist in Abdominal Exploration," in the *Proceedings of the Society of American Gastrointestinal Endoscopic Surgeons (SAGES) Scientific Conference*, Ft. Lauderdale, FL, Apr. 13-16, 2005b.
Rentschler et al., "In Vivo Robots for Laparoscopic Surgery," *Studies in Health Technology and Informatics—Medicine Meets Virtual Reality*, ISO Press, Newport Beach, CA, 2004a, 98: 316-322.
Rentschler et al., "Theoretical and Experimental Analysis of In Vivo Wheeled Mobility," *ASME Design Engineering Technical Conferences: 28th Biennial Mechanisms and Robotics Conference*, Salt Lake City, Utah, Sep. 28-Oct. 2, 2004: 1-9.
Rosen et al., "Spherical Mechanism Analysis of a Surgical Robot for Minimally Invasive Surgery—Analytical and Experimental Approaches," Studies in Health Technology and Informatics—Medicine Meets Virtual Reality, pp. 442-448, Jan. 2005.
Rosen et al., "The BlueDRAGON—A System of Measuring the Kinematics and the Dynamics of Minimally Invasive Surgical Tools In-Vivo," *Proc. of the 2002 IEEE International Conference on Robotics and Automation*, Washington, DC, May 2002: 1876-1881.
Rosen et al., "Task Decomposition of Laparoscopic Surgery for Objective Evaluation of Surgical Residents' Learning Curve Using Hidden Markov Model," *Computer Aided Surgery*, 2002, 7: 49-61.
Rosen et al., "Objective Laparoscopic Skills Assessments of Surgical Residents Using Hidden Markov Models Based on Haptic Information and Tool/Tissue Interactions," *Studies in Health Technology and Informatics—Medicine Meets Virtual Reality*, Jan. 2001.
Ruurda et al., "Feasibility of Robot-Assisted Laparoscopic Surgery," *Surgical Laparoscopy, Endoscopy & Percutaneous Techniques*, 2002, 12(1): 41-45.
Sackier et al., "Robotically assisted laparoscopic surgery," *Surgical Endoscopy*, 1994, 8: 63-66.
Satava, "Surgical Robotics: The Early Chronicles," *Surgical Laparoscopy, Endoscopy & Percutaneous Techniques*, 2002, 12(1): 6-16.
Schurr et al., "Robotics and Telemanipulation Technologies for Endoscopic Surgery," *Surgical Endoscopy*, 2000, 14: 375-381.
Stiff et al., "Long-term Pain: Less Common After Laparoscopic than Open Cholecystectomy," *British Journal of Surgery*, 1994, 81: 1368-1370.
Suzumori et al., "Development of Flexible Microactuator and its Applications to Robotics Mechanisms,"*Proceedings of the IEEE International Conference on Robotics and Automation*, 1991.

Taylor et al., "A Telerobotic Assistant for Laparoscopic Surgery," *IEEE Eng Med Biol*, 1995, 279-87.
Tendick et al., "Applications of Micromechatronics in Minimally Invasive Surgery," *IEEE/ASME Transactions on Mechatronics*, 1998, 3(1): 34-42.
Way et al., "Fundamentals of Laparoscopic Surgery," *Churchill Livingstone Inc.*, 1995, 14 pp.
Rentschler et al., "In vivo Mobile Surgical Robotic Task Assistance," University of Nebraska Medical Center, 1 pg.
Rentschler et al., "Mobile In Vivo Biopsy Robot," *IEEE International Conference on Robotics and Automation*, Orlando, Florida, May 2006, 4155-4160.
Patronik et al., Development of a Tethered Epicardial Crawler for Minimally Invasive Cardiac Therapies, *IEEE*, 2004, 239-240.
Rosen et al., "Force Controlled and Teleoperated Endoscopic, Grasper for Minimally Invasive Surgery—Experimental Performance Evaluation," *IEEE Transactions of Biomedical Engineering*, Oct. 1999, 46(10): 1212-1221.
Salky, "What is the Penetration of Endoscopic Techniques into Surgical Practice?" *Digestive Surgery*, 2000, 17: 422-426.
Dakin et al., "Comparison of laparoscopic skills performance between standard instruments and two surgical robotic systems," *Surg Endosc*, 2003, 17: 574-579.
Nio et al., "Efficiency of manual vs. robotical (Zeus) assisted laparoscopic surgery in the performance of standardized tasks," *Surg Endosc*, 2002, 16: 412-415.
Melvin et al., "Computer-Enhanced vs. Standard Laparoscopic Antireflux Surgery," *J Gastrointest Surg*, 2002, 6: 11-16.
Park et al., "Trocar-less Instrumentation for Laparoscopy: Magnetic Positioning of Intra-abdominal Camera and Retractor," *Ann Surg*, Mar. 2007, 245(3): 379-384.
Peters, "Minimally Invasive Colectomy: Are the Potential Benefits Realized?" *Dis Colon Rectum 1993*, 36: 751-756.
Gong et al., "Wireless endoscopy," *Gastrointestinal Endoscopy*, 2000, 51(6): 725-729.
Bauer et al., "Case Report: Remote Percutaneous Renal Access Using a New Automated Telesurgical Robotic System," *Telemedicine Journal and e-Health* 2001, 4: 341-347.
Kang et al., "Robotic Assistants Aid Surgeons During Minimally Invasive Procedures," *IEEE Engineering in Medicine and Biology*, Jan./Feb. 2001, 94-104.
Breedveld et al., "Design of Steerable Endoscopes to Improve the Visual Perception of Depth During Laparoscopic Surgery," *ASME* , Jan. 2004, 126: 1-5.
Fireman et al., "Diagnosing small bowel Crohn's disease with wireless capsule endoscopy," *Gut* 2003, 52: 390-392.
Abbott et al., "Design of an Endoluminal NOTES Robotic System," *Proceedings of the 2007 IEEE Conference on intelligent Robots and Systems*, 2007, 410-416.
Li et al., (2000), "Microvascular Anastomoses Performed in Rats Using a Microsurgical Telemanipulator," *Comp. Aid. Surg.* 5:326-332.
Southern Surgeons Club, (1991), "A prospective analysis of 1518 laparoscopic cholecystectomies," *N. Engl. J. Med.* 324 (16): 1073-1078.
Wolfe et al, (1991), "Endoscopic Cholecystectomy, An Analysis of Complications," *Arch. Surg.* 126:1192-1196.
Schippers et al., (1996), "Requirements and Possibilities of Computer-Assisted Endoscopic Surgery," *Computer Integrated Surgery: Technology and Clinical Applications*, pp. 561-565.
Kazemier et al., (1998), "Vascular Injuries During Laparoscopy," *J. Am. Coll. Surg.* 186(5):604-5.
Leggett et al., (2002), "Aortic injury during laparoscopic fundoplication—An underreported complication," *Surg. Endoscopy* 16(2):362.
Munro, (2002), "Laparoscopic access: complications, technologies, and techniques," *Curr. Opin. Obstet. Gynecol.*, 14(4):365-74.
Orlando et al., (2003), "Needle and Trocar Injuries in Diagnostic Laparoscopy under Local Anesthesia: What is the True Incidence of These Complications?" *Journal of Laparoendoscopic & Advanced Surgical Techniques* 13(3):181-184.

(56) References Cited

OTHER PUBLICATIONS

Tendick et al., (1993), "Sensing and Manipulation Problems in Endoscopic Surgery: Experiment, Analysis, and Observation," *Presence* 2(1):66-81.
Chanthasopeephan et al., (2003), "Measuring Forces in Liver Cutting: New Equipment and Experimental Results," *Annals of Biomedical Engineering* 31:1372-1382.
U.S. Appl. No. 11/932,441, filed Oct. 31, 2007, entitled "Robot for Surgical Applications," 33 pp.
U.S. Appl. No. 11/947,097, filed Nov. 29, 2007, entitled "Robotic Devices With Agent Delivery Components and Related Methods," 55 pp.
U.S. Appl. No. 12/192,663, filed Aug. 15, 2008.
U.S. Appl. No. 12/324,364, filed Nov. 26, 2008.
Applicant Response to Office Action dated Aug. 21, 2006, in related case U.S. Appl. No. 11/403,756, filed Nov. 21, 2006, 52 pp.
Applicant Response to Office Action dated Aug. 18, 2006, in related case U.S. Appl. No. 11/398,174, filed Nov. 7, 2006, 8 pp.
Examiner Interview Summary dated Nov. 30, 2006, in related case U.S. Appl. No. 11/398,174, 2 pp.
Applicant Response to Office Action dated Oct. 29, 2007, in related case U.S. Appl. No. 11/695,944, filed Jan. 22, 2008, 6 pp.
Applicant Amendment after Notice of Allowance under Rule 312, filed Aug. 25, 2008, in related case U.S. Appl. No. 11/695,944, 6 pp.
U.S. Appl. No. 11/966,741, filed Dec. 28, 2007, entitled "Methods Systems, and Devices for Surgical Visualization and Device Manipulation," 52 pp.
Franzino, "The Laprotek Surgical System and the Next Generation of Robotics," Surg Clin North Am, 2003 83(6): 1317-1320.
Rentschler et al., "Miniature in vivo Robots for Remote and Harsh Environments," IEEE Transactions on Information Technology in Biomedicine, Jan. 2006; 12(1): 66-75.
Olympus, http://www.letsgodigital.org/en/news/articles/story_2150.html, 2004.
"International Search Report and Written Opinion of international application No. PCT/US2007/014567, mailed Apr. 28, 2008, 19 pp.".
Midday, Jeff et al., "Material Handling System for Robotic natural Orifice Surgery", Proceedings of the 2011 Design of medical Devices Conference, Apr. 12-14, 2011, Minneapolis, MN, 4 pages.
International Preliminary Report on Patentability from related case PCT/US2007/014567, mailed Jan. 8, 2009, 11 pp.
International Search report and Written Opinion from international application No. PCT/US2012/41911, mailed Mar. 13, 2013.
International Search Report and Written Opinion from international application No. PCT/US12/46274, mailed Sep. 25, 2012.
International Search Report and Written Opinion from international application No. PCT/US2007/089191, mailed Nov. 10, 2008, 20 pp.
"International Search Report and Written Opinion from international application No. PCT/US07/14567, mailed Apr. 28, 2008, 19 pp.".
International Search Report and Written Opinion of international application No. PCT/US2008/069822, mailed Aug. 5, 2009, 12 pp.
International Search Report and Written Opinion of international application No. PCT/US2008/073334, mailed Jan. 12, 2009, 11 pp.
International Search Report and Written Opinion of international application No. PCT/US2008/073369, mailed Nov. 12, 2008, 12 pp.
International Search Report and Written Opinion issued in PCT/US11/46809, mailed Dec. 8, 2011.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine model," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.

Kang et al., "Robotic Assistants Aid Surgeons During Minimally Invasive Procedures," IEEE Engineering in Medicine and Biology, Jan.-Feb. 2001; pp. 94-104.
Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.
Kazemier et al. (1998), "Vascular Injuries During Laparoscopy," J. Am. Coli. Surg. 186(5): 604-5.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136:180-184.
Leggett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
MacFarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, 1/4-inch VGA NTSC/PAL CMOS Digital Image Sensor, 98 pp.
Midday Jeff et al., "Material Handling System for Robotic natural Orifice Surgery", Proceedings of the 2011 Design of medical Devices Conference, Apr. 12-14, 2011, Minneapolis, MN, 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Office Action dated Apr. 17, 2007, received in related case U.S. Appl. No. 11/552,379, 5 pp.
Office Action dated Apr. 3, 2009, received in related case U.S. Appl. No. 11/932,516, 43 pp.
Office Action dated Aug. 18, 2006, received in related case U.S. Appl. No. 11/398,174, 6 pp.
Office Action dated Aug. 21, 2006, received in related case U.S. Appl. No. 11/403,756, 6 pp.

(56) References Cited

OTHER PUBLICATIONS

Office Action dated Oct. 29, 2007, received in related case U.S. Appl. No. 11/695,944, 6 pp.
Office Action dated Oct. 9, 2008, received in related case U.S. Appl. No. 11/932,441, 4 pp.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What is the True Incidence of These Complications?" Journal of Laparoendoscopic & Advanced Surgical Techniques 13(3): 181-184.
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Applicant Amendment after Notice of Allowance under Rule 312, filed Aug. 25, 2008, in related case U.S. Appl. No. 11/695,944, 6pp.
Applicant Response to Office Action dated Apr. 17, 2007, in related case U.S. Appl. No. 11/552,379, filed Aug. 8, 2007, 7 pp.
Applicant Response to Office Action dated Aug. 18, 2006, in related case U.S. Appl. No. 11/398,174, filed Nov. 7, 2006, 8pp.
Applicant Response to Office Action dated Aug. 21, 2006, in related case U.S. Appl. No. 11/403,756, filed Nov. 21, 2006, 52pp.
Applicant Response to Office Action dated Oct. 29, 2007, in related case U.S. Appl. No. 11/695,944, filed Jan. 22, 2008, 6pp.
Atmel 8OC5X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.

Camarillo et al., "Robotic Technology in Surgery: Past, Present and Future," The American Journal of Surgery, 2004; 188: 2S-15S.
Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al., (2003), "Measuring Forces in Liver Cutting: New Equipment and Experimenal Results," Annals of Biomedical Engineering 31: 1372-1382.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving in Vivo Robot Visioin Quality," from the Proceedings of Medicine Meets Virtual Realtiy, Long Beach, CA, Jan. 26-29, 2005. 1 pg.
Dumpert et al., "Stereoscopic In Vivo Surgical Robots," IEEE Sensors Special Issue on In Vivo Sensors for Medicine, Jan. 2007, 10 pp.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2pp.
Falcone et al., "Robotic Surgery," Clin. Obstet. Gynecol. 2003, 46(1): 37-43.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Flynn et al., "Tomorrow's Surgery: micromotors and microbots for minimally invasive procedures," Minimally Invasive Surgery & Allied Technologies.
Franklin et al., "Prospective Comparison of Open vs. Laparoscopic Colon Surgery for Carcinoma: Five-Year Results," Dis Colon Rectum, 1996; 39: S35-S46.
Franzino, "The Laprotek Surgical System and the Next Generation of Robotics," Surg Clin North Am, 2003 83(6).
Fraulob et al., "Miniature assistance module for robot-assisted heart surgery," Biomed. Tech. 2002, 47 Suppl. 1, Pt. 1:12-15.
Fukuda et al, "Mechanism and Swimming Experiment of Micro Mobile Robot in Water," Proceedings of the 1994 IEEE International Conference on Robotics and Automation, 1994: 814-819.
Fukuda et al, "Micro Active Catheter System with Multi Degrees of Freedom," Proceedings of the IEEE International Conference on Robotics and Automation, May, 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Grady, "Doctors Try New Surgery for Gallbladder Removal," The New York Times, Apr. 20, 2007, 3 pp.
Guber et al., "Miniaturized Instrumetn Systems for Minimally Invasive Diagnosis and Therapy," Biomedizinishe Technic. 2002, Band 47, Erganmngsband 1.

(56) References Cited

OTHER PUBLICATIONS

Tendick et al., "Applications of Micromechatronics in Minimally Invasive Surgery," IEEE/ASME Transactions on Mechatronics, 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Way et al., (editors), "Fundamentals of Laparoscopic Surgery," Churchill Livingstone Inc., 1995, 14 pp.
Wolfe et al., "Endoscopic Cholecystectomy: An analysis of Complications," Arch. Surg. Oct. 1991; 126: 1192-1196.
Worn et al., "Espirit Project No. 33915: Miniaturised Robot for Micro Manipulation (MINIMAN)", Nov. 1998; http://www.ipr.ira.ujka.de/-microbot/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy A Breakthrough Diagnostic Tool for Small Intestine Imagining," vol. 25, No. 1, Gastroenterology Nursing, pp. 24-27.
International Search Report and Written Opinion of international application No. PCT/US2010/061137, mailed Feb. 11, 2011, 10 pp.
Abbou et al., "Laparoscopic Radical Prostatectomy with a Remote Controlled Robot," The Journal of Urology, Jun. 2001, 165: 1964-1966.
Glukhovsky et al.., "The development and application of wireless capsule endoscopy," Int. J. Med. Robot. Comput. Assist. Surgery, 2004; I (1): 114-123.
Gong et al., "Wireless endoscopy," Gastrointestinal Endoscopy 2000; 51(6): 725-729.
Hanly et al., "Value of the SAGES Learning Center in introducing new technology," Surgical Endoscopy, 2004; 19 (4): 477-483.
Hanly et al., "Robotic Abdominal Surgery," The American Journal of Surgery 188 (Suppl.to Oct. 1994): 19S-26S, 2004.
Patronik et al., "Development of a Tethered Epicardial Crawler for Minimally Invasive Cardiac Therapies," IEEE, pp. 239-240.
Patronik et al., "Crawling on the Heart: A Mobile Robotic Device for Minimally Invasive Cardiac Interventions," MICCAI, 2004, pp. 9-16.
Patronik et al., "Preliminary evaluation of a mobile robotic device for navigation and intervention on the beating heart," Computer Aided Surgery, 10(4): 225-232, Jul. 2005.
Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al., "Analysis and Development of Locomotion Devices for the Gastrointestinal Tract," IEEE Transaction on Biomedical Engineering, vol. 49, No. 6, Jun. 2002, pp. 613-616.
Phee et al., "Development of Microrobotic Devices for Locomotion in the Human Gastrointestinal Tract," International Conference on Computational Intelligence, Robotics and Autonomous Systems (CIRAS 2001), Nov. 28-30, (2001), Singapore.
Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, 1 pg.

Preliminary Amendment filed Apr. 11, 2007, in related case U.S. Appl. No. 11/403,756, 7 pp.
Preliminary Amendment filed Jul. 30, 2008, in related case U.S. Appl. No. 12/171,413, 4 pp.
RCE and Amendment filed Jun. 13, 2007, in related case U.S. Appl. No. 11/403,756, 8 pp.
Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006e.
Rentschler et al., "Mobile In Vivo Biopsy Robot," IEEE International Conference on Robotics and Automation, Orlando, Florida, May 2006, pp. 4155-4160.
Rentschler et al, "Miniature in vivo Robots for Remote and Harsh Environments," IEEE Transactions on Information Technology in Biomedicine, Jan. 2006; 12(1): 66-75.
Rentschler et al., "An In Vivo Mobile Robot for Surgical Vision and Task Assistance," Journal of Medical Devices, Mar. 2007, vol. 1: 23-29.
Rentschler et al., "In vivo Mobile Surgical Robotic Task Assistance," 1 pg.
Rentschler et al., "In vivo Robotics during the NEEMO 9 Mission," Medicine Meets Virtual Reality, Feb. 2007, 1 pg.
Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.
Rentschler et al., "Mechanical Design of Robotic In Vivo Wheeled Mobility," ASME Journal of Mechanical Design, 2006a, pp. 1-11.
Rentschler et al., "Mobile In Vivo Camera Robots Provide Sole Visual Feedback for Abdominal Exploration and Cholecystectomy," Journal of Surgical Endoscopy, 20-1: 135-138, 2006b.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler et al., "Natural Orifice Surgery with an Endoluminal Mobile Robot," The Society of American Gastrointestinal Endoscopic Surgeons, Dallas, TX, Apr. 2006d, 14 pp.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9
Rentschler et al., "Toward In Vivo Mobility," Studies in Health Technology and Infonnatics—Medicine Meets Virtual Reality, ISO Press, Long Beach, CA, 2005a, III: 397-403.
Response to Rule 312 Amendment in related case U.S. Appl. No. 11/695,944, dated Jan. 12, 2009, 2 pp.
Riviere et al., "Toward Active Tremor Canceling in Handheld Microsurgical Instruments," IEEE Transactions on Robotics and Automation, Oct. 2003, 19(5): 793-800.
Rosen et al., "Force Controlled and Teleoperated Endoscopic, Grasper for Minimally Invasive Surgery—Experimental Performance Evaluation," IEEE Transactions of Biomedical Engineering, Oct. 1999; 46(10): 1212-1221.
Rosen et al., "Objective Laparoscopic Skills Assessments of Surgical Residents Using Hidden Markov Models Based on Haptic Information and Tool/Tissue Interactions," Studies in Health Technology and Infonnatics—Medicine Meets Virtual Reality, Jan. 2001, 7 pp.
Rosen et al., "Spherical Mechanism Analysis of a Surgical Robot for Minimally Invasive Surgery—Analytical and Experimental Approaches," Studies in Health Technology and Infonnatics—Medicine Meets Virtual Reality, pp. 442-448, Jan. 2005.
Rosen et al., "Task Decomposition of Laparoscopic Surgery for Objective Evaluation of Surgical Residents'Learning Curve Using Hidden Markov Model," Computer Aided Surgery, vol. 7, pp. 49-61, 2002.
Rosen et al., "The Blue DRAGON—A System of Measuring the Kinematics and the Dynamics of Minimally Invasive Surgical Tools

(56) References Cited

OTHER PUBLICATIONS

In-Vivo," Proc. of the 2002 IEEE International Conference on Robotics and Automation, Washington, DC, pp. 1876-1881, May 2002.
Ruurda et al., "Robot-Assisted surgical systems: a new era in laparoscopic surgery," Ann R. Coll Surg Engl., 2002; 84: 223-226.
Ruurda et al., "Feasibility of Robot-Assisted Laparoscopic Surgery," Surgical Laparoscopy, Endoscopy & Percutaneous Techniques, 2002; 12(1):41-45.
Sackier et al., "Robotically assisted laparoscopic surgery," Surgical Endoscopy, 1994; 8: 63-66.
Salky, "What is the Penetration of Endoscopic Techniques into Surgical Practice?" Digestive Surgery, 2000; 17:422-426.
Satava, "Surgical Robotics: The Early Chronicles," Surgical Laparoscopy, Endoscopy & Percutaneous Techniques, 2002; 12(1): 6-16.
Schippers et al., (1996) "Requirements and Possibilities of Computer-Assisted Endoscopic Surgery," In: Computer Integrated Surgery: Technology and Clinical Applications, pp. 561-565.
Schurr et al., "Robotics and Telemanipulation Technologies for Endoscopic Surgery," Surgical Endoscopy, 2000; 14: 375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fantastic Voyage: Smart Pill to Expand Testing," http://www.smartpilldiagnostics.com, Apr. 13, 2005, 1 pg.
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al.., "Long-term Pain: Less Common After Laparoscopic than Open Cholecystectomy," British Journal of Surgery, 1994; 81: 1368-1370.
Strong, et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-287.
Tendick et al.. (1993), "Sensing and Manipulation Problems in Endoscopic Surgery: Experiment, Analysis, and Observation," Presence 2( 1): 66-81.
Palm, William, "Rapid Prototyping Primer" May 1998 (revised Jul. 30, 2002) (http://www.me.psu.edu/lamancusa/rapidpro/primer/chapter2.htm).
Stoianovici et al., "Robotic Tools for Minimally Invasive Urologic Surgery", Jan. 1, 2002, pp. 1-17.
Cleary et al., "State of the Art in Surgical Rootics: Clinical Applications and Technology Challenges", "Computer Aided Surgery", Jan. 1, 2002, pp. 312-328, vol. 6.
Green, "Telepresence Surgery", Jan. 1, 1995, Publisher: IEEE Engineering in Medicine and Biology.

\* cited by examiner

METHODS, SYSTEMS, AND DEVICES FOR SURGICAL VISUALIZATION AND DEVICE MANIPULATION

CROSS-REFERENCE TO RELATED APPLICATION(S)

This application claims priority to U.S. Provisional Patent Application Ser. No. 60/890,691, filed Feb. 20, 2007 and titled "Methods, Systems, and Devices for Surgical Visualization and Device Manipulation;" U.S. Provisional Patent Application Ser. No. 60/956,032, filed Aug. 15, 2007 and titled "Methods, Systems, Devices of Robotic Medical Procedures;" and U.S. Provisional Patent Application Ser. No. 60/983,445, filed Oct. 29, 2007 and titled "Methods and Systems for Instructor and Student Operation of Surgical Devices," all of which are hereby incorporated herein by reference in their entireties.

FIELD OF THE INVENTION

The present invention relates to a console for use in surgical procedures. More specifically, the console includes external manipulation components and a visual display that can be used in conjunction with an internal robotic device to minimize trauma to a patient during surgery.

BACKGROUND OF THE INVENTION

Open surgeries often require a surgeon to make sizable incisions to a patient's body in order to have adequate visual and physical access to the site requiring treatment. The application of laparoscopy for performing procedures, such as abdominal procedures, marks a paradigm shift in general surgery. Laparoscopic surgeries are performed using small incisions in the abdominal wall and inserting a small endoscope into the abdominal cavity and transmitting the images captured by the endoscope onto a visual display. The surgeon can thus see the abdominal cavity without making a sizable incision in the patient's body, reducing invasiveness and providing patients with the benefits of reduced trauma, shortened recovery times, and improved cosmetic results. In addition to the endoscope, laparoscopic surgeries are performed using long, rigid tools inserted through incisions in the abdominal wall. However, conventional techniques and tools for performing laparoscopic procedures can limit the dexterity and vision of the surgeon. Given the size of the incisions, the maneuverability of the tools is limited and additional incisions may be required if an auxiliary view of the surgical site is needed. In addition, the typical location of the visual display necessitates the surgeon gazing in an upward and frontal direction. The visual acuity of the surgeon may also be limited by the two-dimensional video display. These constraints in both dexterous ability and vision limit the application of laparoscopic techniques to less complicated procedures.

Another method currently used in minimally invasive surgeries relates to translumenal procedures. Traditional translumenal procedures utilize modified conventional endoscopic tools. However, these modified endoscopic tools present constraints similar to laparoscopic tools, including a diminished visual field and the use of a two-dimensional visual display. Also, because the endoscopic tools must be flexible along their length in order to access the body cavity through a natural orifice, they present the additional challenges of determining and maintaining spatial orientation. In addition, tissue manipulations are limited due to the necessity of applying force along the axis of the endoscope.

Thus, there is a need in the art for improved, minimally invasive surgical devices.

BRIEF SUMMARY

In a first aspect, a surgical device includes a console having a visual display and a device manipulation component, a robotic device having a camera and a connection component. The robotic device is configured to be positioned completely within a body cavity. The camera is configured to transmit visual images to the visual display. The connection component operably couples the console component and the robotic device. The device manipulation component is positioned relative to the visual display so as to appear to be penetrating the visual display.

In another aspect, a surgical system includes a console component having a visual component and a manipulator, a robotic device having a camera for providing visual images to the visual component and a connection component. The robotic device is position-able entirely within a body cavity. The connection component is operably coupled to the console component and configured to be coupleable to the robotic device when the robotic device is disposed within the body cavity. The manipulator is positioned relative to the visual component so as to appear to be penetrating the visual component.

Yet another aspect is a method of performing a minimally invasive surgery. The method includes positioning a console component at a location relative to a body cavity, inserting a robotic device through a natural orifice of a patient and into a passage connected to the natural orifice, passing the robotic device through the passage and into the body cavity such that the robotic device is located substantially completely within the body cavity, transmitting visual images captured by the robotic device to the console component, displaying the visual images on a visual display, providing inputs based on movements of manipulation components operatively connected to the console component and the robotic device based on the visual images on the visual display, and correspondingly moving the robotic device based on the inputs and the movements of the manipulation components. The visual display is positioned relative to the body cavity such that the body cavity appears visually to a user to be viewable directly through the visual display.

DETAILED DESCRIPTION

Figure 1A:
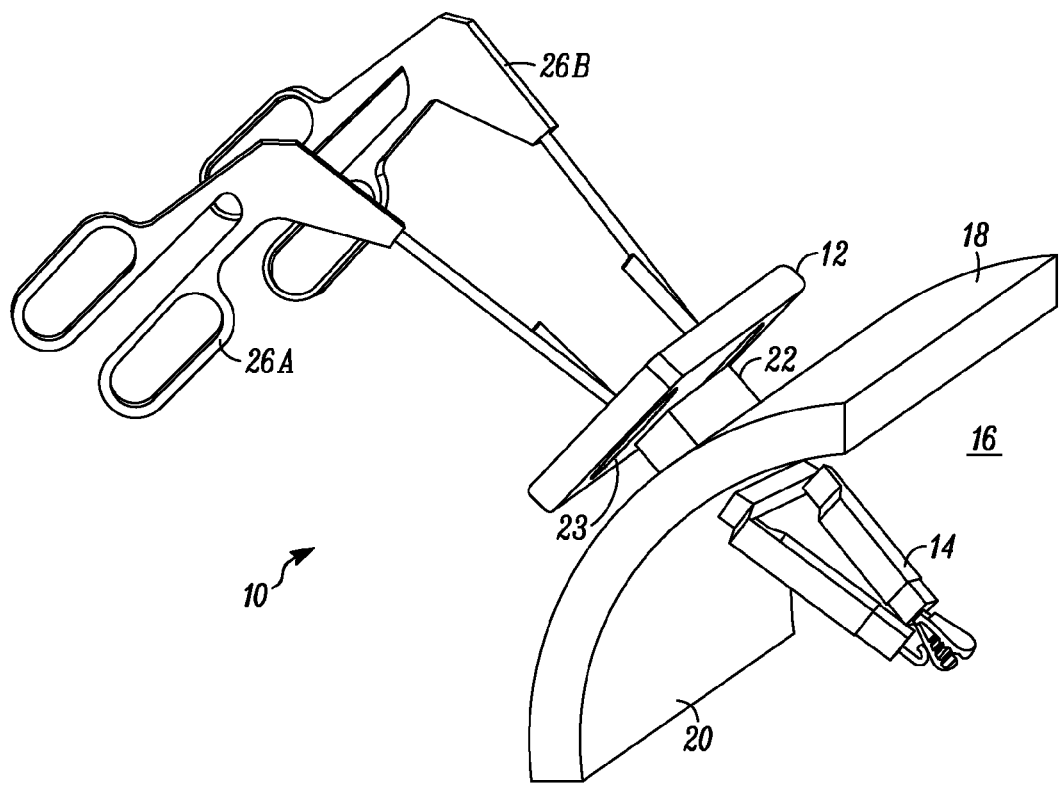
FIG. 1A is a perspective view of a surgical visualization and device manipulation system, according to one embodiment.
Figure 1B:
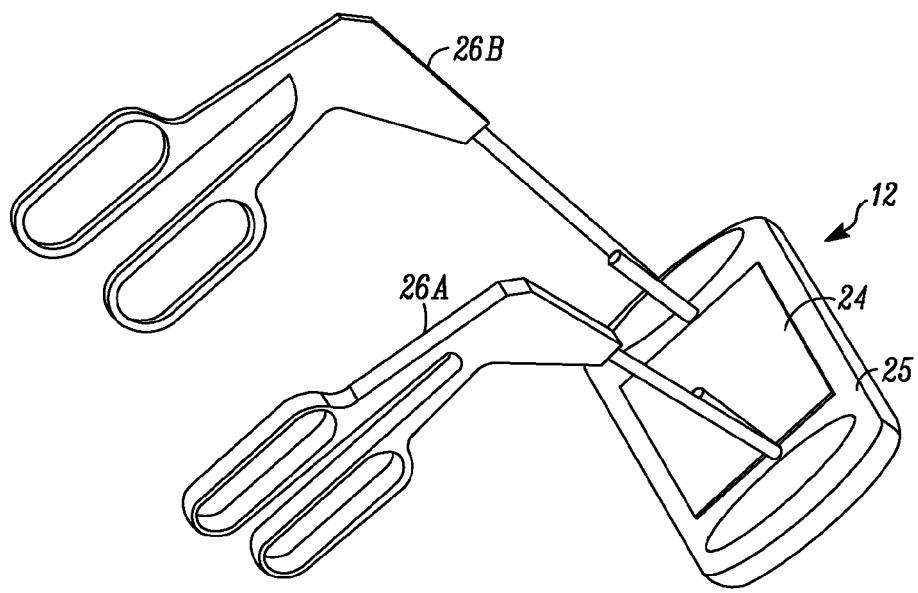
FIG. 1B is a perspective view of the surgical visualization and device manipulation system, according to the embodiment of FIG. 1A.

FIGS. 1A and 1B are perspective views of one embodiment of a surgical visualization and device manipulation system 10. System 10 includes a control console 12 that operates in conjunction with robotic surgical device 14 positioned inside body cavity 16, such as an abdomen, of a patient. That is, the control console 12 can be used to operate the device 14 inside the body cavity 16. System 10 addresses the visual and dexterous manipulation constraints associated with standard surgical procedures, such as laparoscopic and natural orifice translumenal endoscopic surgical ("NOTES") procedures, while building upon the established skill set of laparoscopic surgeons. Robotic device 14 is located entirely within body cavity 16 and (in contrast to traditional laparoscopic and endoscopic tools) is not constrained by an entry incision.

In accordance with the implementation depicted in FIGS. 1A and 1B, console 12 is configured to be positioned outside body cavity 16 of the patient and includes console magnet 22, a visual display 24 (best depicted in FIG. 1B), and first manipulator 26A and second manipulator 26B (collectively referred to as "manipulators 26"). As used herein, "console" is intended to mean a controller or operational hub. Console magnet 22 draws robotic device 14 toward internal cavity wall 20 of body cavity 16 and adjacent console 12, thereby positioning robotic device 14 against internal cavity wall 20. Visual display 24 is coupled to robotic device 14 and displays visual feedback of body cavity 16 captured by robotic device 14. In this embodiment, manipulators 26 are connected to console 12, and in conjunction with console 12, communicate with and control robotic device 14. In the implementation as depicted, console 12 and manipulators 26 operate robotic device 14 via wireless communication. Alternatively, as explained in further detail below, the console 12 can be coupled to the robotic device 14 via a physical connection.

In one implementation, by positioning robotic device 14 within body cavity 16 relative to console 12, system 10 allows the surgeon to determine and maintain spatial orientation of robotic device 14 with respect to console 12. Other benefits of system 10 can include, but are not limited to: providing a training tool for surgeons, reducing or eliminating the need for a surgeon to be on-site, and reducing the cost of robotic surgical systems.

FIG. 1B shows a perspective view of console 12 with manipulators 26 according to one embodiment. As used herein, "manipulator" is intended to mean any input device associated with a console for operating a robotic device via a wired or wireless connection component. A manipulator can also be referred to herein as a "manipulator arm" or "manipulator handle." In this embodiment, each manipulator 26A and 26B is configured to provide for three rotations (one axially, two cross-axially) and one translation (up and down) as well as a binary trigger for controlling such operational components as graspers, cauterization components, and/or suction/irrigation components. These capabilities will be explained in further detail in additional embodiments herein. The positions of manipulators 26 are measured and the information is transferred to a system processor (not shown) disposed within the console 12 which processes the position information and transmits resulting commands to robotic device 14 to position the device 14 or any device connected to the robotic device 14 in the appropriate position or location. The positions of manipulators 26 are continuously updated to the processor such that the commands and the resulting corresponding movements of manipulators 26 and robotic device 14 and/or any device connected to robotic device 14 are substantially in real-time.

In an exemplary embodiment as shown, manipulators 26 substantially replicate standard laparoscopic tool handles. That is, manipulators 26 have generally the same shape and movement as standard laparoscopic tools. Alternatively, manipulators 26 can take various forms, including, but not limited to: computer controls known in the art such as 2-dimensional and 3-dimensional mice and keyboards; heavy equipment and airline controls known in the art such as sticks, wheels, and triggers; and various techniques used in virtual reality involving smart gloves or other similar devices made to fit the human body and model human motion. In one embodiment, for example, virtual reality control is used and robotic device 14 is modified to look more human. In another embodiment, robotic device 14 is configured to look like a surgeon's hands.

According to one implementation, visual display 24 is positioned on a front face 25 of console 12 opposite rear face 23. In practice, console 12 is positioned on external surface 18 of body cavity 16 such that front face 25 and visual display 24 of console 12 are visible to a surgeon standing over body cavity 16. In one aspect, visual display 24 is operably coupled to an image capturing component on robotic device 14. Signals from robotic device 14 may be transmitted in any format (e.g., NTSC, digital, PAL, etc.) to visual display 24 of console 12. For example, the signal may be a video signal and/or a still image signal. Visual display 24 may also be any known image display component capable of displaying the images collected by an image capturing component that can be used with robotic device 14. In one embodiment, visual display 24 is a standard video monitor. In an alternative embodiment, the visual display 24 can display two dimensional visual feedback, three dimensional visual feedback or stereoscopic imaging to a surgeon via imaging component on robotic device 14. Those of ordinary skill in the art will recognize that a signal from a camera can be processed to produce a display signal for many different types of display devices, including, but not limited to: televisions configured to display an NTSC signal, televisions configured to display a PAL signal, cathode ray tube based computer monitors, LCD monitors, and plasma displays. In an exemplary embodiment, console 12 is a da Vinci® console, available from Intuitive Surgical, Inc., located in Sunnyvale, Calif.

In practice, as shown in FIGS. 1A and 1B, console 12 is located according to one embodiment on external surface 18 of body cavity 16, while robotic device 14 is positioned such that the device 14 can be positioned or controlled by console 12. In the embodiment of FIG. 1A, robotic device 14 is positioned against internal cavity wall 20 of body cavity 16. This configuration allows console 12 and robotic device 14 to be unconstrained by the entry incision while providing the surgeon with a view of the surgical area. Console 12 can be used to control the robotic device 14 and further can move along the external surface 18 while robotic device remains substantially fixed with respect to the console 12 such that robotic device 14 moves within the patient (such as along internal cavity wall 20) and can be positioned at a desired location within body cavity 16 and provide the user with alternative views and workspaces.

Figure 2A:
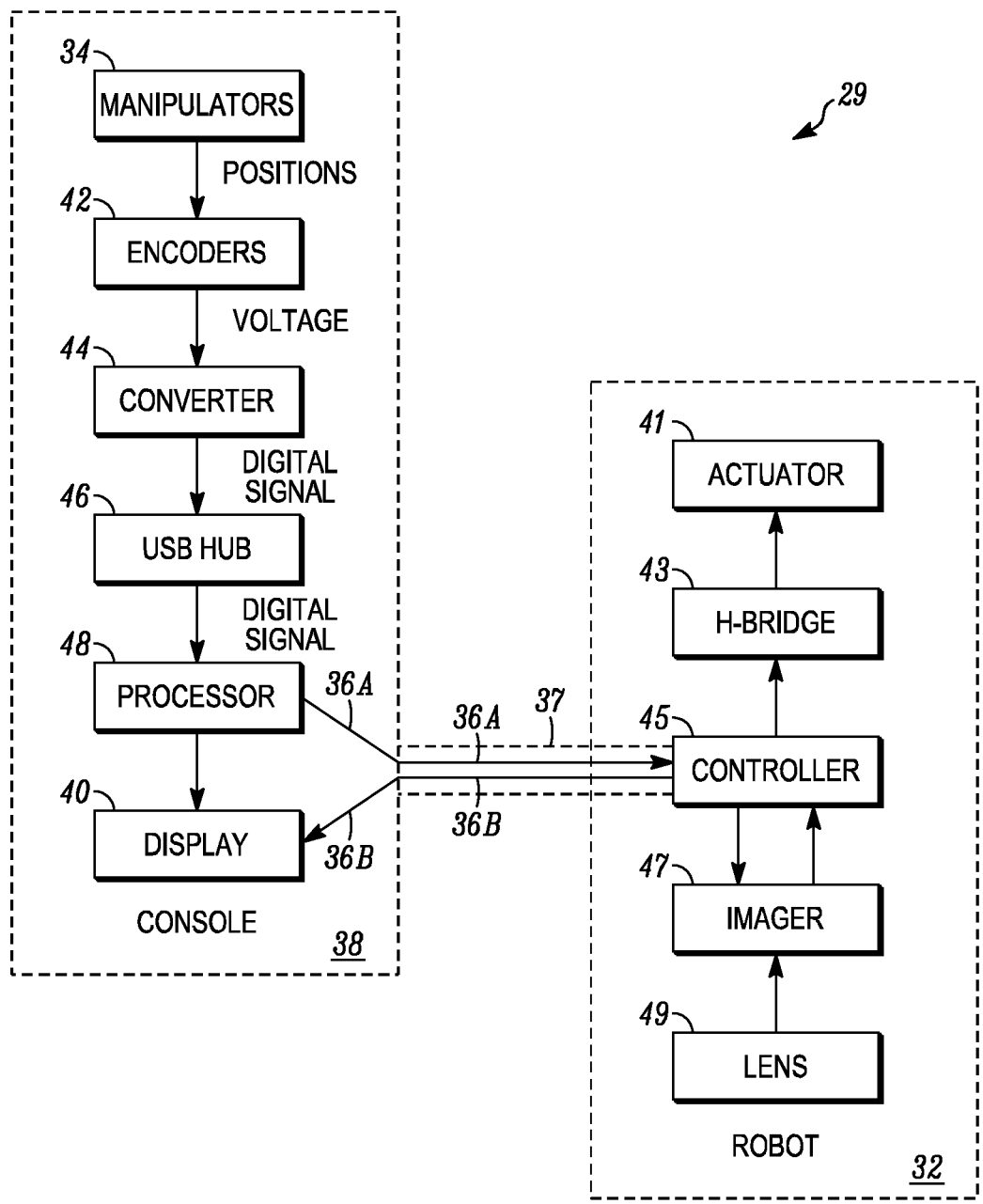
FIG. 2A is a diagram of a control scheme of the surgical visualization and device manipulation system, according to one embodiment.

FIG. 2A depicts a schematic diagram of the internal components of a further embodiment of a surgical visualization and device manipulation system 29. Robotic device 32 is connected to manipulators 34 via connection component 37, which connects robotic device 32 to console 38. As used herein, "connection component" is intended to mean a wired or wireless connection between at least two components of a surgical visualization and device manipulation system that provides for the transmission and/or exchange of information and/or power between components. Connection component 37 operably couples console 38 and robotic device 32 to allow for communication between (1) imaging component (not shown) of robotic device 32 and visual display 40 on console 38, such that images collected by imaging component (not shown) can be transmitted to console 38 and displayed on visual display 40, and/or (2) manipulators 34 and robotic device 32, such that manipulation of manipulators 34 by the user results in operation or control of robotic device 32.

According to one embodiment, connection component 37 is a wired connection such as a wire, cord, or other physical flexible coupling. The wired connection is coupled at one end to robotic device 32 and at a second end to console 38 (and particularly, to manipulators 34). For purposes of this application, the physical or wired connection can also be referred to as "tethered" or "a tether." The wired connection can be any physical component that is flexible, pliable, or otherwise capable of being easily formed or manipulated into different shapes or configurations. According to one embodiment, the wired connection includes one or more wires or cords or any other type of physical component operably coupled to the device 32 and console 38. The wired connection is configured to transmit or convey power and/or data 36A, video 36B, or anything else necessary or useful for operation of robotic device 32. In a further alternative, the wired connection comprises at least two wires or cords or other such components, each of which are connected to a separate external unit (which, in one example, are a power source and a data transmission and receiver unit as described below).

Figure 2B:
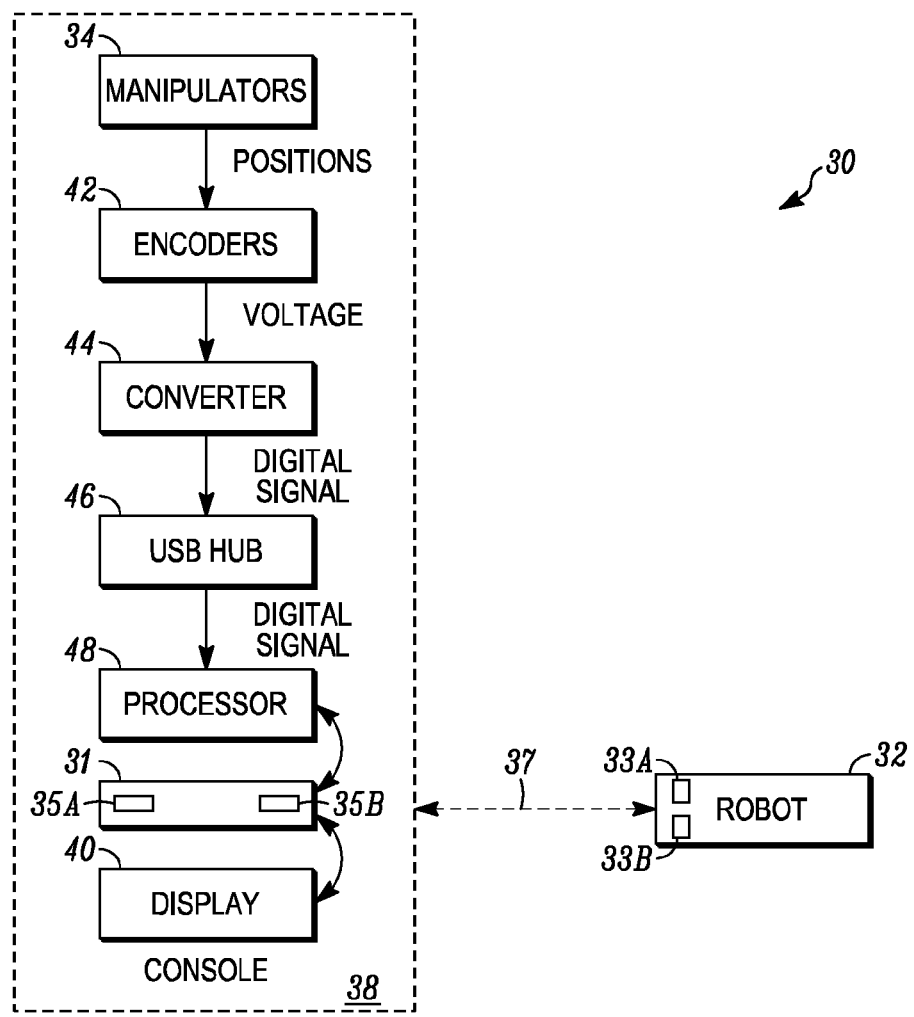
FIG. 2B is a diagram of an alternative control scheme of the surgical visualization and device manipulation system, according to one embodiment.

FIG. 2B depicts a schematic diagram of an alternative embodiment of a surgical visualization and device manipulation system 30 in which connection component 37 is a wireless connection. That is, in this embodiment, the robotic device 32 communicates wirelessly with console 38 (and thus visual display 40 and manipulators 34). The wireless connection can also be referred to herein as "untethered." An "untethered device," "wireless device," or "wireless connection" is intended for purposes of this application to mean any robotic device 32 that is fully enclosed within the patient's body such that no portion of robotic device 32 is external to the patient's body for at least a portion of the surgical procedure or, alternatively, any robotic device 32 that operates within the patient's body while not being physically connected to any external object for at least a portion of the surgical procedure. In one embodiment, an untethered robotic device 32 transmits and receives data wirelessly, including data required for controlling robotic device 32. In the wireless embodiment shown in FIG. 2B, robotic device 32 has an internal power supply, along with a receiver 33A and transmitter 33B for wireless connection. In this embodiment the console 38 has an internal power supply, along with a receiver 35A and transmitter 35B for wireless connection. Alternatively, the console 38 can be powered using an external power supply such as a wall outlet. The console 38, receiver 35A, and transmitter 35B form a communication component 31 that is linked to the processor 48 and display 40. The receivers 33A and 35A and transmitters 33B and 35B used with a wireless robotic device 32 as described herein can be any known receiver and/or transmitter. For example, any known receiver and/or transmitter used in remote vehicle locking devices, remote controls and mobile phones. In an exemplary embodiment, robot commands are transmitted/received using a 900 MHz wireless transceiver chip (NRF905-REEL), available from Nordic Semiconductor, located in Sunnyvale, Calif., and video is transmitted using a 2.4 GHz transmitter (LUV200M), available from Spyville.com, located in Monterey, Tenn.

Figure 3A:
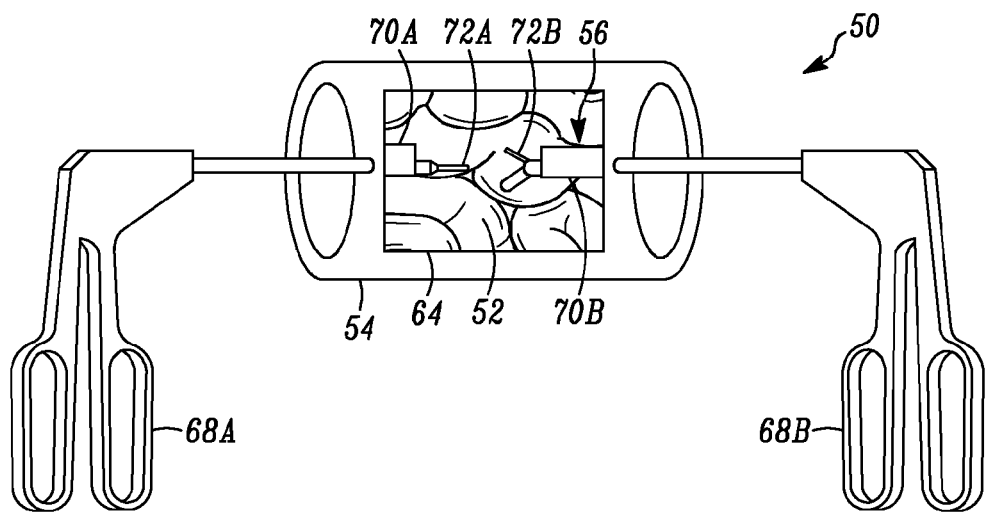
FIG. 3A is a top view of a surgical visualization and device manipulation system positioned relative to a body cavity of a patient, according to another embodiment.
Figure 3B:
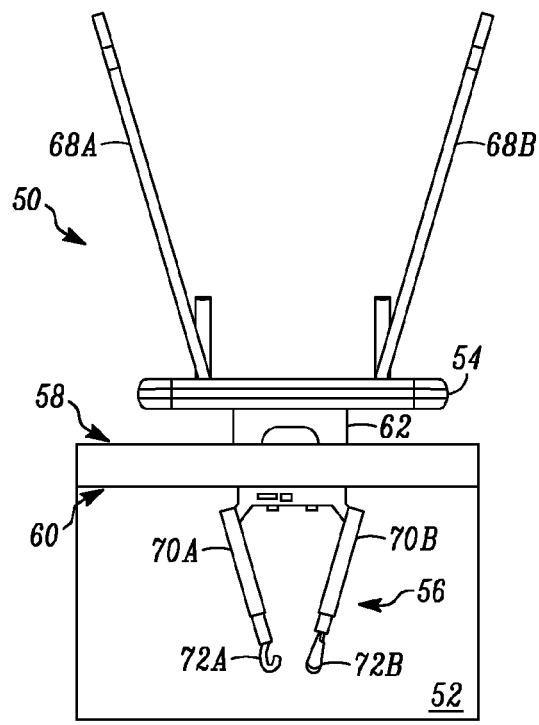
FIG. 3B is a front view of the surgical visualization and device manipulation system positioned relative to a body cavity of the patient, according to the embodiment of FIG. 3A.
Figure 3C:
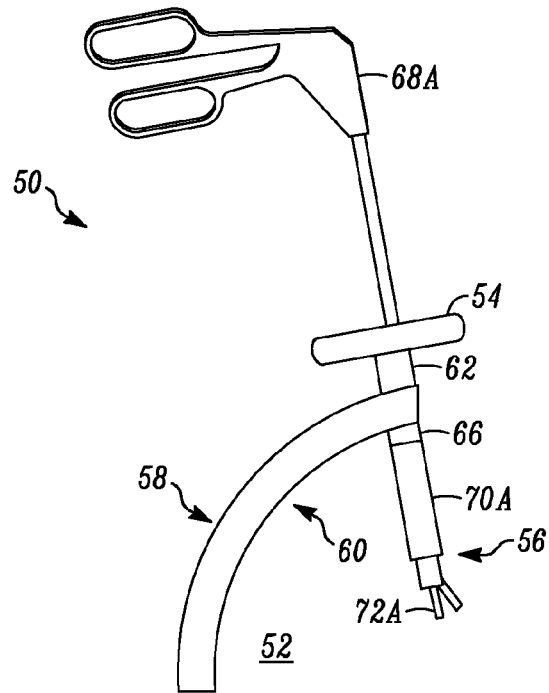
FIG. 3C is a side view of the surgical visualization and device manipulation system positioned relative to a body cavity of the patient, according to the embodiment of FIG. 3A.

FIGS. 3A, 3B, and 3C show a top view, a front view and a side view, respectively, of a further embodiment of a system 50 positioned with respect to body cavity 52 of a patient. System 50 includes console 54 and robotic device 56 and creates a "virtual hole" or "virtual incision" effect when console 54 is positioned on external surface 58 of body cavity 52 and robotic device 56 is held against internal surface 60 within body cavity 52 by console magnet 62. That is, visual display 64 shows the visual image being collected by imaging component 66 of robotic device 56 within the patient's body cavity 52 on console 54 and manipulators 68 are positioned relative to visual display 64 such that first manipulator 68A and second manipulator 68B (collectively referred to as "manipulators 68") appear from the user's perspective to be penetrating visual display 64 and body cavity 52 of a patient as best shown in FIG. 3A. The resulting effect for the user or surgeon is that the user has the impression that he is looking directly into body cavity 52 and that he can operate manipulators 68 to directly control first arm 70A and second arm 70B (collectively referred to as "arms 70") and first end effector 72A and second end effector 72B (collectively referred to as "end effectors 72") of robotic device 56 disposed within body cavity 52. Console 54 is thus able to replicate open surgery by locating visual display 64 in front of the user and over body cavity 52 while manipulators 68 are at the hands of the user. The location of visual display 64 is similar to the standard practice in non-robotic laparoscopic surgery, thereby adding to the realistic aspect of the "virtual hole." In addition, this positioning of console 54, visual display 64, manipulators 68, arms 70 and end effectors 72 provides a more comfortable, ergonomically correct relationship between the gaze direction of the user and the surgical site or task location. Using system 50, manipulators 68 positioned on or near the patient's body seem to mirror or substantially duplicate the look and feel of standard laparoscopic tool handles for the user, thereby building upon the existing experience of laparoscopic surgeons and making the use of system 50 more intuitive. As a result, a surgeon or other user experienced with standard procedures can easily begin using system 50 without much acclimation or training required, if any at all.

In one embodiment the robot is controlled in an open-loop system in which the surgeon uses the console to command the robot movement without any arm or end-effector position feedback except for video feedback from the imaging system. One example of an open-loop control scheme relates to using the manipulators 68 to simply toggle between moving and stationary positions. In this scheme, the robotic arms can only move at one speed and are either commanded to move or not move. Therefore, the manipulators 68 can be moved in a direction to engage the robotic arms to begin moving. The manipulators 68 can then be moved back to the original position to stop the robotic arms from moving.

The system depicted in FIG. 2A utilizes another open-loop control scheme. The positions of manipulators 34 in this embodiment are measured using potentiometers 42. A "potentiometer" can also be referred to as an "encoder." Other methods for measuring the manipulator position include optical encoders that use infrared light or other wavelengths in the spectrum or acoustical encoders that measure sound. As used herein, "encoder" is intended to mean any device that is capable of converting rotary or translational position to electronic pulses. Position data from the encoder measurements allows for determining the position of each manipulator relative to the console and velocities of the manipulators. This information can then be used to determine commands for the robotic arms.

In FIG. 2A, each manipulator 34A and 34B in this embodiment includes three rotations (one axially, two cross-axially) and one translation (up and down). Each of these motions are measured. In this embodiment, the encoder position is transmitted as a digital signal to a processor. Alternatively, the encoder position is transmitted as an analog voltage. In this alternative embodiment, the encoder voltages outputted by the encoders 42 are then transmitted to an analog-to-digital converter 44 before being sent to the processor 48. In one example shown in FIG. 2A, the analog signals are digitized at 1000 Hz. These digitized signals are then transferred, via a universal serial bus (USB) hub 46, to a processor 48. The software in processor 48 reads the positions of manipulators 34 (as a digital signal) from the USB hub 46 and determines the motor commands to be sent to robotic device 32. In this embodiment, the encoder position indicates if the robot arm should move and in what direction. This results in a binary control system in which the actuation motors in the robot are commanded as "full on" forward, "full on" backwards, or off. For example, arms on the robot (not shown) can be either commanded to move in a specified direction, or not to move. There is no direct feedback from the actuators to the control program in computer 48. Commands from computer 48 are sent to the actuators of robotic device 32 via a cable that tethers robotic device 32 to computer 48. In another embodiment, the converter/USB hub/computer are all integrated into the console so that the robot has a single tether from the console. In a further alternative embodiment, the tether is removed and replace by a wireless system that transmits commands to the robot and video from the robot to the console wirelessly as depicted in FIG. 2B. In this wireless embodiment, the robot includes an onboard power source such as a battery. In either the wired (FIG. 2A) or wireless (FIG. 2B) embodiment, the commands received by the controller 45 are sent to an H-bridge 43 to provide a pulse width modulated (PWM) signal to the actuators 41. The PWM signal represents the percentage of full operating power at which the motor is instructed to operate. In this embodiment, the only feedback from the robot to the console is the video image from the imager system (including the imager 47 and lens 49) onboard the robot 32. The NTSC video signal from imaging component 47 of robotic device 32 is sent back through the cable to visual display 40 on console 38. In this open-loop configuration, no robot position data is returned to the computer control program. The surgeon observes what is happening to the robotic device by observing the display and this observation allows the surgeon to command the robot to move in the direction desired.

In a further alternative, the controller is a "closed-loop" controller system commonly used in robotic technologies. As is understood, a closed-loop controller system is a system with a controller that allows the user to provide specific instructions regarding a specific movement or action and further provides for a feedback sensor that senses when the device completes the specific movement or action. This system allows for very specific instructions or commands and very precise actions. For example, in the embodiment in FIG. 3, the user may input instructions into the controller that the device 56 should position the right arm 70B at a 30° angle with respect to the body 66, and the right arm 70B then moves until the sensor senses that the arm 70B is positioned at the desired angle. The feedback sensor can be a joint sensor, a visual sensor, or any other known feedback sensor. A closed-loop controller system thus allows for utilizing very specific and precise control of a device, including very precise device positioning, trajectory control, and force control. In one embodiment, the device could then be precisely operated in joint space or Cartesian space. In this embodiment, the position of the manipulator and the robot arm can be scaled so that the surgeon has finer control at the robot end effector.

In addition, various control schemes are contemplated with respect to the end effectors as well. For example, according to one embodiment, each manipulator 68A and 68B includes a trigger for grasping, cauterization, suction/irrigation, or some other action at a device operational component. In one embodiment, the trigger is binary and is used to turn cauterization, grasping, suction, or irrigation on or off in an open-loop manner. Alternatively, the positional feedback from the operational component and/or trigger is used to control the operational component in a closed-loop manner so that the operational component closely matches input from the surgeon.

Alternatively, the robotic device 56 may be controlled by any one of a number of control schemes in addition to those described above, and the various types of manipulators 68 that are available further broaden the options available for the interaction between the manipulators 68 and the robotic device 56. In one embodiment, manipulators 68 are used like typical joystick controllers such that repositioning (including rotation or translation) of either controller from a nominal position causes an arm or component of the robotic device 56 to move in the corresponding direction. In this embodiment, the velocity of motion of robotic device 56 or at least one of its components (such as an arm) is controlled by the magnitude of the input applied to manipulators 68, whereby increased rotation or movement of manipulators 68 causes robotic device 56 or its components to move more rapidly.

It is understood that any of the above control schemes and any other known robotic controller technologies can be incorporated into any of the robotic devices disclosed herein.

According to another implementation, any robotic device described herein is connected via a connection component not only to a console, but also to an external unit (i.e. a power source and a data transmission and receiver unit) or one or more other robotic devices, such robotic devices being either as described herein or otherwise known in the art. That is, according to one embodiment, two or more robotic devices can be operably coupled to each other as well as to an external unit. According to one embodiment in which there are two robotic devices, the two robotic devices are operably coupled to each other and an external unit by a flexible wired connection or a wireless connection. That is, the two robotic devices are operably coupled to each other by a flexible wired connection that is coupled to each robotic device and each robotic device is also operably coupled to an external unit by a flexible wired connection. In one embodiment, there are three separate flexible wired connections: (1) a wired connection connecting the two robotic devices, (2) a wired connection connecting one of the robotic devices to an external unit, and (3) a wired connection connecting the other of the robotic devices to the external unit. Alternatively, one wired connection is operably coupled to both robotic devices and an external unit. In a further alternative, any number of wired connection may be used in any configuration to provide for connection of two robotic devices to each other and an external unit.

Alternatively, the two or more robotic devices are operably coupled to each other as well as an external unit in an untethered fashion. That is, the robotic devices are operably coupled to each other and an external unit in a fashion such that they are not physically connected. In one embodiment, the robotic devices and the external unit are operably coupled wirelessly.

Alternatively, the visual display and manipulators need not be in physical contact or physically adjacent to each other. That is, in one embodiment, the visual display and the manipulators may be in completely different locations. In an exemplary embodiment, the visual display may be positioned at eye level of the user such that the user need only look straight ahead, while the manipulators are positioned adjacent to the patient's body or elsewhere. Those skilled in the art will appreciate that the location of the visual display may be anywhere within the view of the surgeon.

In a further embodiment, the console also does not need to be disposed in proximity with the patient, or the robotic device. That is, a console as described herein may be at a completely different geographical location and still be capable of operating in conjunction with a robotic device via a connection component to perform a procedure on a patient. In an extreme example, a surgeon could perform a surgery using a visualization and control system on a patient in a space station orbiting the earth in which the surgeon on earth operates on the patient by controlling manipulators while looking at visual display, thereby operating a robotic device disposed within the patient in the space station. In such an embodiment, the robotic device can be positioned in the patient using a magnetic component or some other type of attachment component that is positioned in an appropriate location outside the patient's body. Further, it is understood that the surgeon or user, despite being a different geographical location in relation to the patient, can utilize the console in a fashion that substantially replicates or recreates the general "look and feel" of a standard laparoscopic procedure. That is, the user can position the console with the manipulators in front of the user on a table or other object such that the user is positioned in generally the same fashion and utilizes the manipulators in generally the same fashion as if the user were in the same room as the patient and performing a standard laparoscopic procedure on that patient.

Figure 4A:
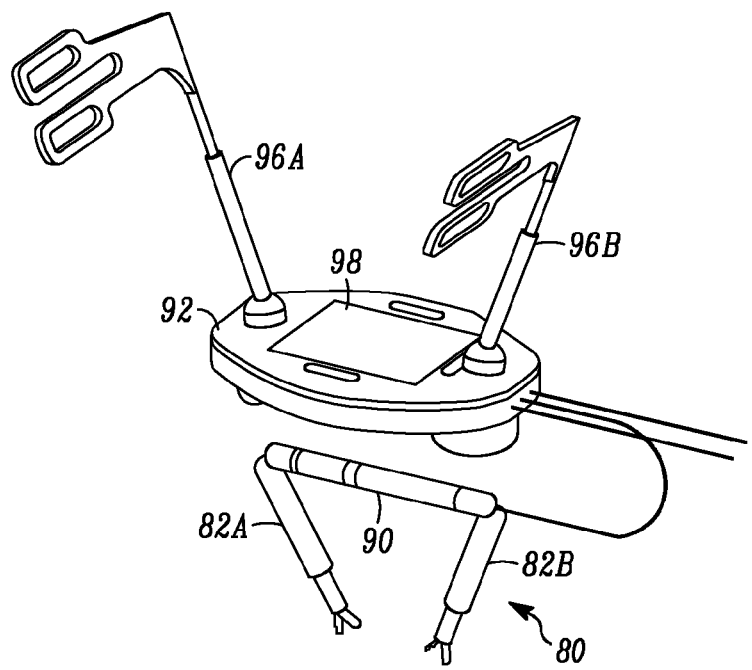
FIG. 4A is a perspective view of a surgical visualization and device manipulation system, according to a further embodiment.
Figure 4B:
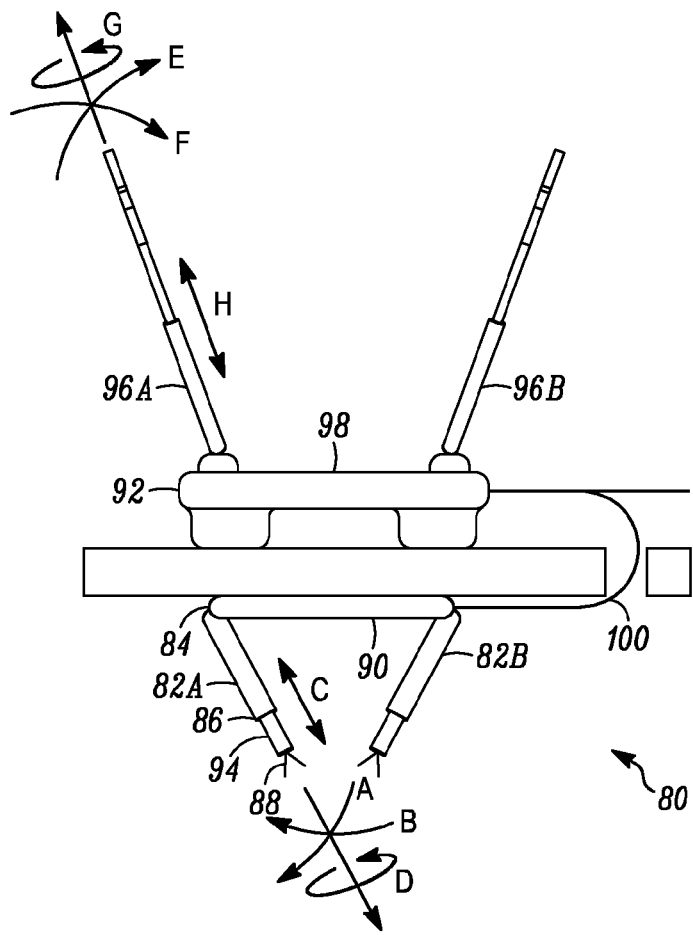
FIG. 4B is a front view of the surgical visualization and device manipulation system, according to the embodiment of FIG. 4A.

A further embodiment of a visualization and device manipulation system 80 is depicted in FIGS. 4A and 4B having a console 92 that can be used to operate a robotic device 80. The robotic device 80 has two arms 82A, 82B (also referred to jointly as "82"). The use of two arms 82 allows the device 80 to perform various procedures and tasks such as stretching and/or dissection tasks.

In accordance with one implementation, each arm 82 can have an operational component (also referred to as an "end effector") such as the operational component 88 coupled to arm 82A. In the embodiment as shown in FIGS. 4A and 4B, the end effector 88 is a grasper 88. Further, the robotic device 80 also has a camera 90. As such, the robotic device 80 of this embodiment can provide for surgical vision and tissue manipulation.

The console 92 is coupled with the robotic device 80 by a connection component 100 that, according to one embodiment, provides one or more of power, command signals, and video. The console 92 includes a display component 98 and two manipulators 96A and 96B (also referred to herein as "joysticks") that can be used to control the movement of the robotic arms 82 via operational coupling between each handle 96 and the corresponding arm 82. Various controls in the form of switches, knobs, or any other type of input components (not shown) on the console 92 can be provided to allow the surgeon to control such things as camera focusing/zoom, illumination levels, panning position of the camera 50, and/or any other components or controllable variables relating to the robotic device 80.

In one exemplary embodiment, the joysticks 96 are configured to operate or "feel" to the surgeon like a standard laparoscopic tool. That is, the surgeon can move the joystick 96 in 4 degrees of freedom ("DOF"), just as standard laparoscopic tools inserted through trocar ports can typically move in four DOF (3 rotations and 1 translation). As shown in FIG. 4B, three of the DOF displayed by the manipulators 96 are rotations that include two off-axis rotations as depicted by arrows E and F and one axial rotation identified by arrow G. The fourth DOF as depicted by arrow H is a translation that allows the surgeon to extend the joystick. In this embodiment, the position of joystick 96 is constrained to move only in these 4 orientations, and the position of the joystick 96 can be measured using a series of encoders coupled to the joystick 96 and the console 92. Using these positions, the control algorithms in the computer system (not shown) in the console 92 determine the actuator commands and transmit those commands to the robotic device 90. Each of the arms 82 in this embodiment as shown in FIG. 4B also allow the surgeon 4 DOF. That is, each arm 82 has a rotational shoulder joint 84 that provides two degrees of freedom as shown by arrows A and B, and a prismatic and rotational elbow joint 86 that provides arm extension and rotation as shown by arrows C and D, respectively. Thus, the robotic device 80 receives the command signals from the console 92 and actuates the appropriate arm 82 to move in the 4 DOF in response to the similar movement caused by the user in the corresponding manipulator 96.

Figure 5A:
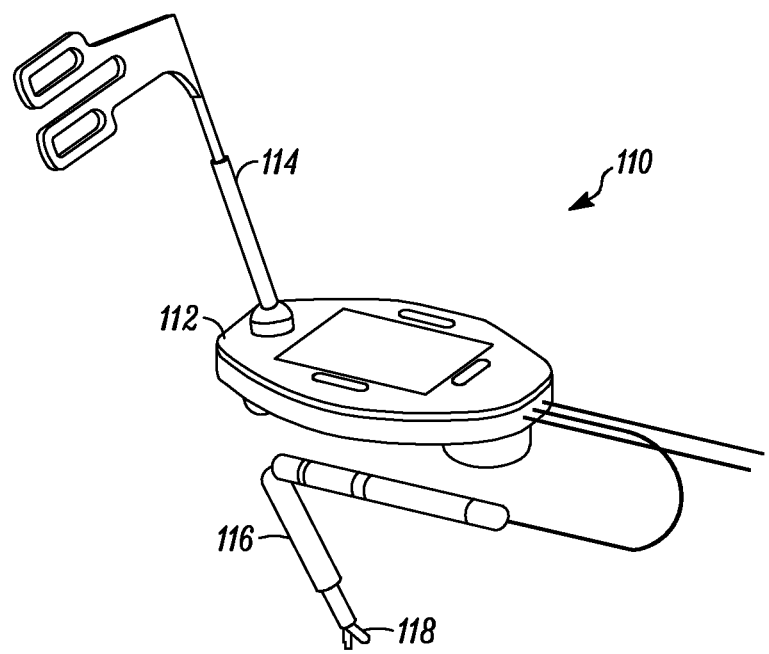
FIG. 5A is a perspective view of a surgical visualization and device manipulation system, according to another embodiment.
Figure 5B:
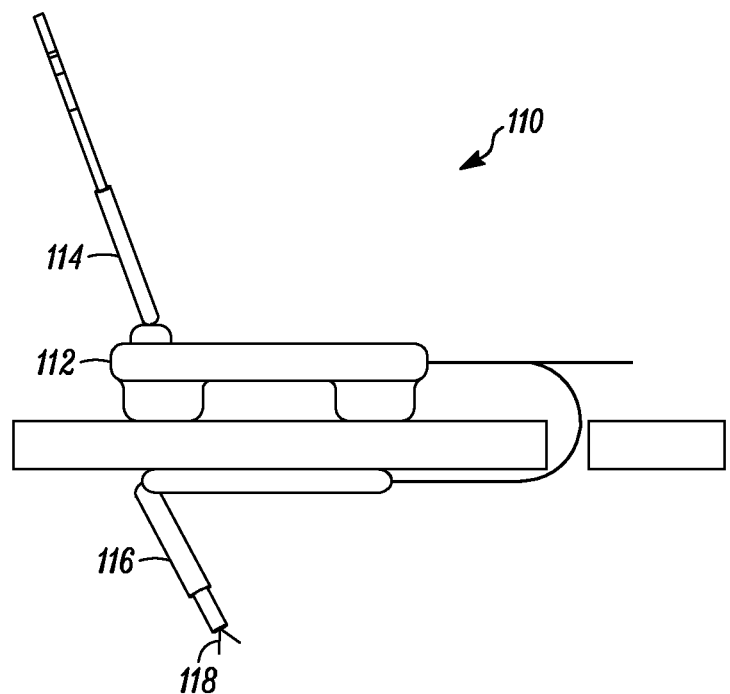
FIG. 5B is a front view of the surgical visualization and device manipulation system, according to the embodiment of FIG. 5A.

FIGS. 5A and 5B depict another embodiment of a visualization and device manipulation system 110 in which the console 112 has a single manipulator arm 114 that controls a single robotic arm 116. According to one implementation, the one-armed robotic device 110 can be used for a variety of surgical procedures and tasks including, but not limited to, tissue biopsy and tissue retraction. For example, the grasper 118 can be used to retract the gall bladder during a cholecystectomy procedure.

Figure 6A:
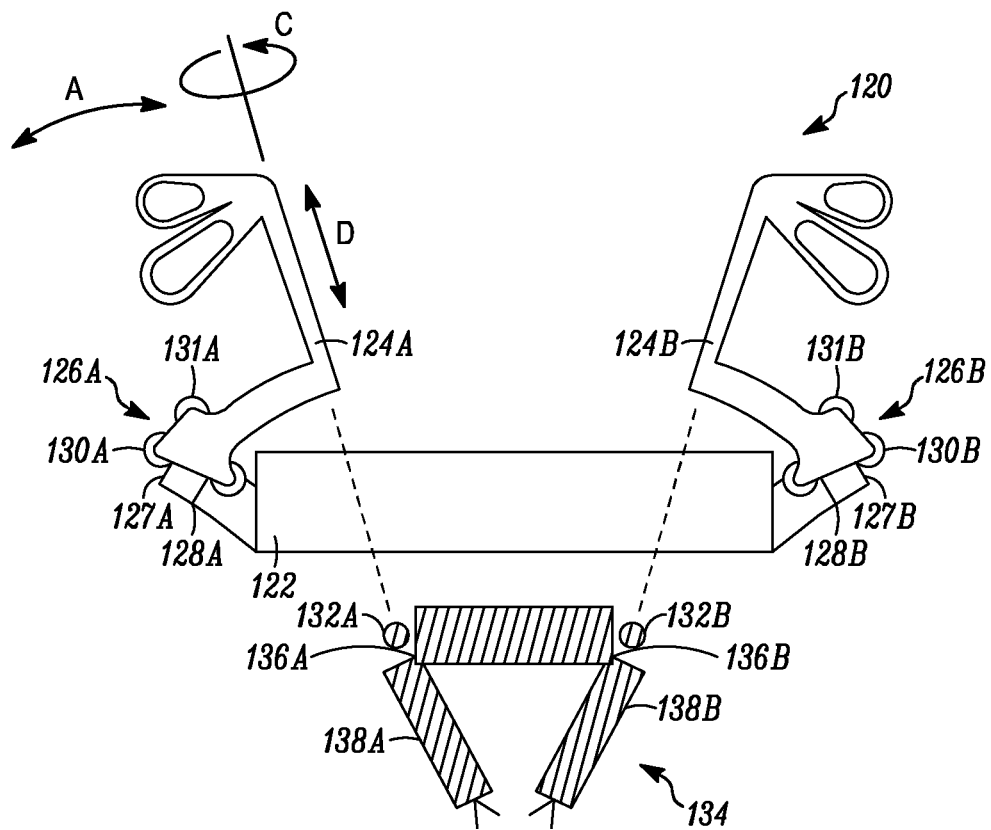
FIG. 6A is a front view of a console and manipulator arms of a surgical visualization and device manipulation system, according to one embodiment.
Figure 6B:
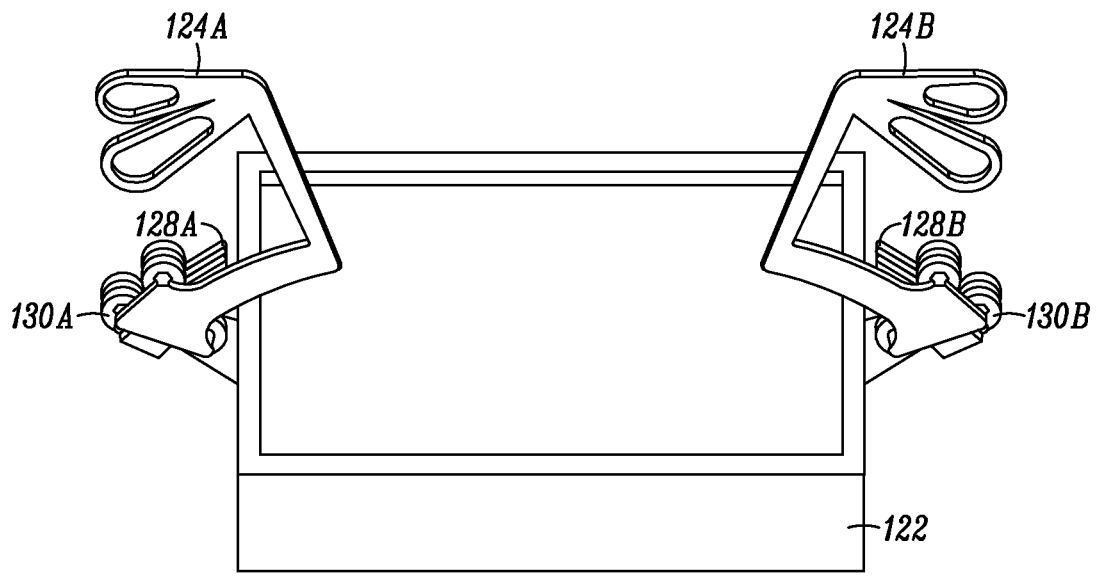
FIG. 6B is a perspective view of the console and manipulator arms of the surgical visualization and device manipulation system, according to the embodiment of FIG. 6A.
Figure 6C:
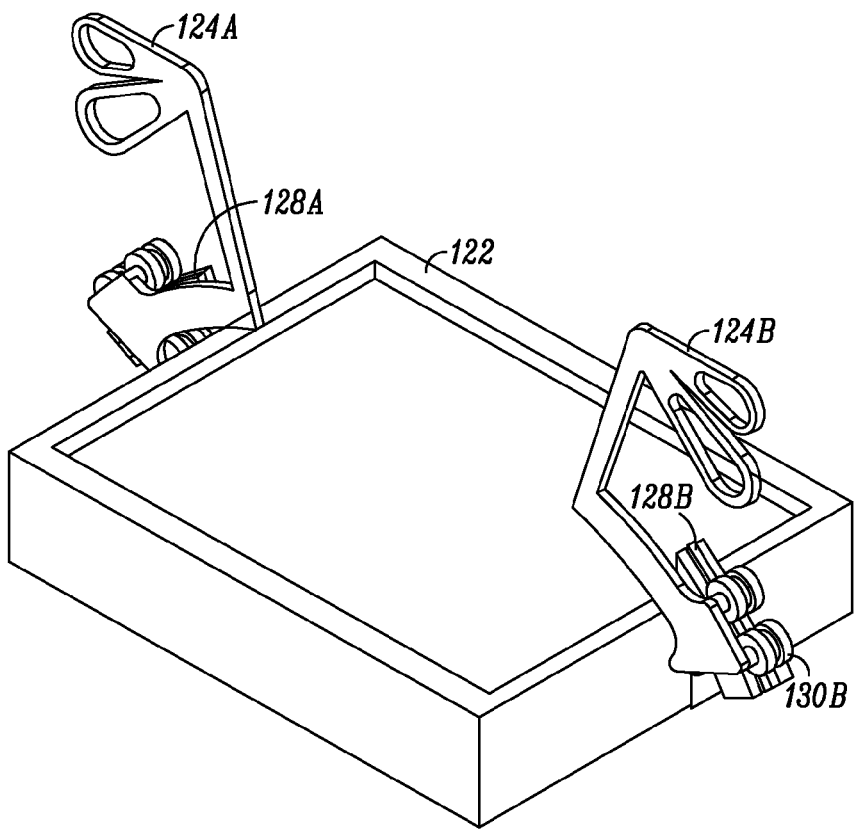
FIG. 6C is a perspective view of the console and manipulator arms of the surgical visualization and device manipulation system, according to the embodiment of FIG. 6A.
Figure 6D:
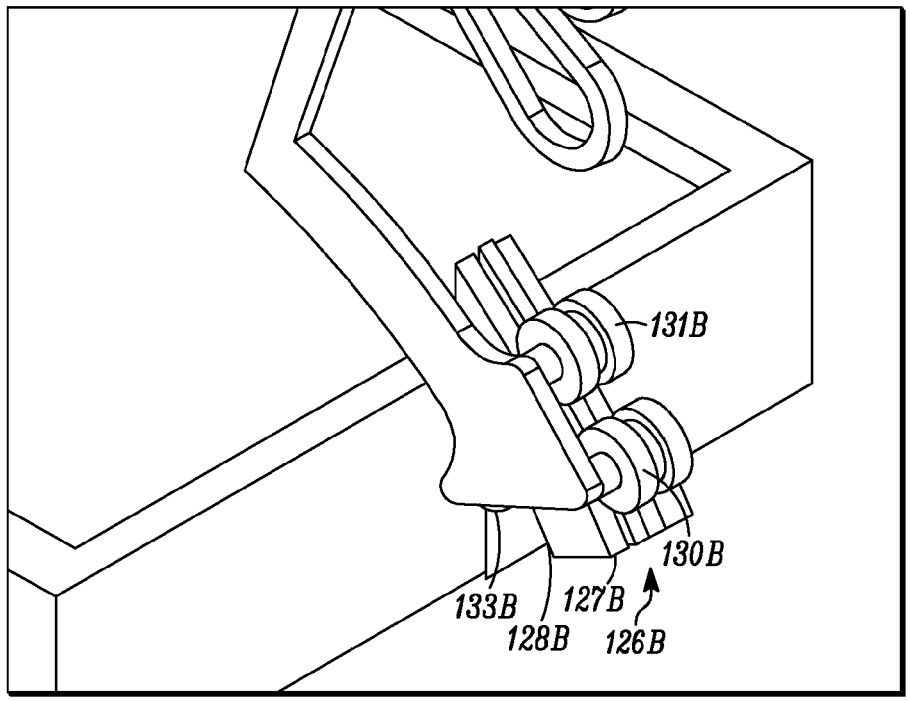
FIG. 6D is an enlarged perspective view of the console and manipulator arms of the surgical visualization and device manipulation system, according to the embodiment of FIG. 6A.

FIGS. 6A, 6B, 6C, and 6D depict an alternative implementation of a visualization and device manipulation system 120. FIG. 6A shows a front view of console 122 having manipulators 124A, 124B (collectively referred to as "manipulators 124"). In this embodiment, each manipulator 124A, 124B is coupled to the console 122 with a carriage system 126A, 126B respectively (collectively referred to as "carriage systems 126"). FIGS. 6B and 6C show two different perspective views of manipulators 124 attached to console 122 by carriage system 126 and FIG. 6D shows an enlarged perspective view of carriage system 126B. As best shown in FIGS. 6A and 6D, each carriage system 126 includes two tracks 127, 128 and three carriage wheels 130, 131, 133. As shown in FIGS. 6A-6D, tracks 127, 128 are fixed to console 122 and connect manipulators 124 to console 122. Each manipulator 124 has three carriage wheels 130, 131, 133 that are in contact with the tracks 127, 128—two upper wheels 130, 131 in contact with the upper track 127 and one lower wheel 133 in contact with the lower track 128. The upper and lower tracks 127, 128 as shown in FIGS. 6A through 6D are positioned at a predetermined angle with respect to the console 122 such that the movement of the wheels 130, 131, 133 along the tracks 127, 128 causes each of the manipulators 124 to rotate about an approximated axis 132 if the arms of the manipulators 124 were extended through and beyond the console (which according to certain embodiments would mean extending into the patient). In one embodiment, the approximated axis 132A, 132B of each manipulator 124A, 124B is coincident with or otherwise in generally the same location as the actual shoulder joints 136A, 136B of robotic device 134 such that the manipulators 124 "seem" to the user to be directly connected to the robotic arms 138A, 138B.

In an alternative implementation, the components of the carriage systems can be reversed such that the tracks are coupled to the manipulators and the wheels are coupled to the console. In this embodiment, the carriage wheels 130 rotate while track 128 moves about an approximated axis 132 as shown in FIG. 1.

Although FIGS. 6A-6D depict carriage system 126 as including one set of tracks 128 and carriage wheels 130 in one plane, in alternative embodiments the carriage system may include any number of sets of tracks and carriage wheels in any number of planes. In one embodiment, the track is not held rigidly to the console, but is instead attached to a second set of carriage wheels. This second set of carriage wheels is then affixed to a second track that is attached to the console. In this embodiment, the first track/carriage wheel assembly allows for one rotation, while the second track/carriage wheel assembly allows for a second rotation. This combination provides both off-axis rotations that are common for laparoscopic surgical instruments during surgery.

Figure 7A:
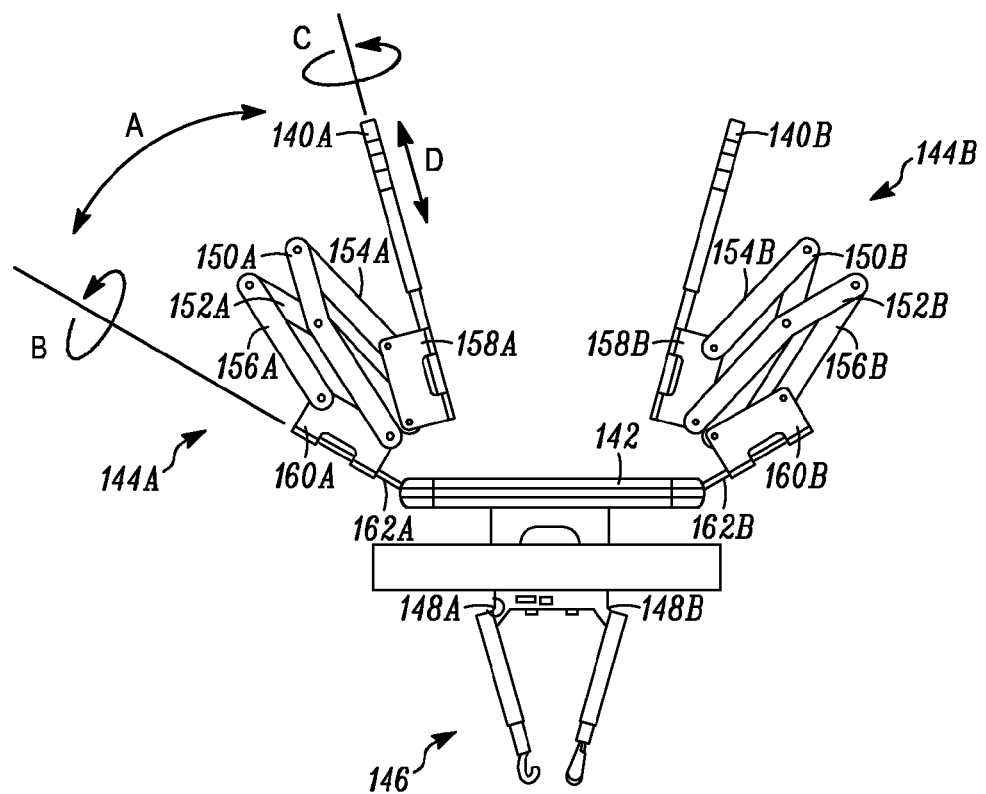
FIG. 7A is a front view of a set of offset planar hinge joint manipulators of a surgical visualization and device manipulation system, according to one embodiment.
Figure 7B:
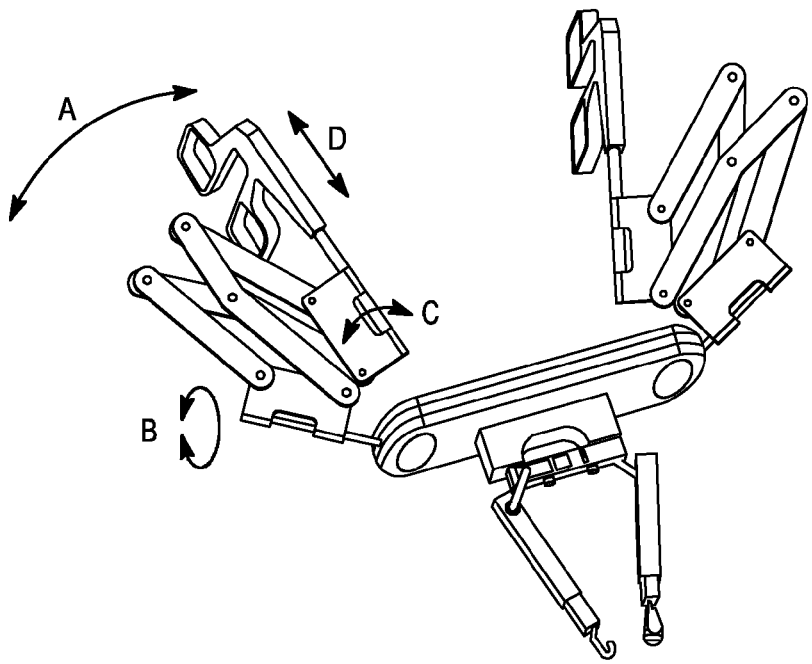
FIG. 7B is a perspective view of the set of the offset planar hinge joint manipulators of the surgical visualization and device manipulation system, according to the embodiment of FIG. 7A.
Figure 7C:
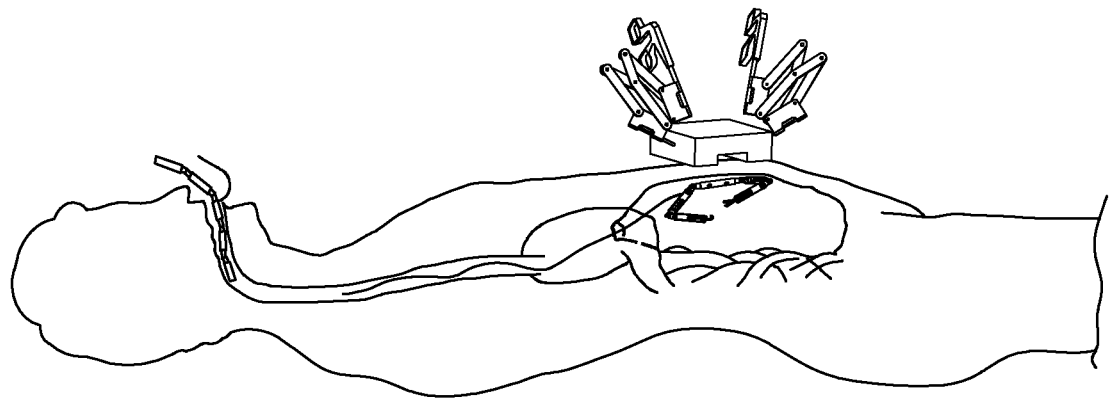
FIG. 7C is a schematic view of the set of the offset planar hinge joint manipulators of the surgical visualization and device manipulation system positioned relative to a body cavity of a patient, according to the embodiment of FIG. 7A.

In another alternative embodiment, manipulators 140A, 140B (collectively referred to as "manipulators 140") may be connected to console 142 by offset planar hinge joints 144A, 144B as shown in FIGS. 7A, 7B, and 7C. It is understood that offset planar hinge joints have been used in the field of micro manipulation and further in the field of parallel robotics where multiple hinges are joined together to form concentric multilink spherical joints. According to one implementation, natural and realistic control of robotic device 146 is achieved by configuring each manipulator 140 to rotate about an approximated axis that is located generally at around the same location as the respective shoulder joints 148A, 148B of robotic device 146. Thus, the use of the offset planar hinge joints 144 allows for two off-axis rotations that generally replicate the rotations common for laparoscopic surgical instruments.

In one embodiment, offset planar hinge joints 144 are six-bar linkages including first bent bracket 150A, 150B and second bent bracket 152A, 152B (collectively referred to as "bent brackets 150, 152"), first straight bracket 154A, 154B and second straight bracket 156A, 156B (collectively referred to as "straight brackets 154, 156") and horizontal leaf 158A, 158B and base leaf 160A, 160B (collectively referred to as "leaves 158, 160"). Leaves 158, 160 are similar to door hinges because they allow for rotation about a single axis. Horizontal leaves 158A, 158B allow the manipulators 140 to rotate axially as indicated by arrow C and translate up and down as indicated by arrow D. Base leaves 160A, 160B are also free to rotate as indicated by arrow B about fixed pins 162A, 162B. The six-bar linkage allows manipulators 140 to rotate along arrow A about the approximated remote axis located generally in the same area as the device shoulder joints 148. These combined three rotations allow for the look and feel of traditional laparoscopy while the console 142 and robot 146 are not physically connected.

The offset planar hinge joint configuration as depicted in FIGS. 7A, 7B, and 7C allows for rotation of the manipulators 140 about an approximated axis of rotation located generally in about the same location as the robotic device shoulder joints 148. This kinematic configuration has been implemented in other machine designs much like common levers. In this embodiment, the approximated axis of rotation of each manipulator 140 being located generally at shoulder joints 148 causes the motion of manipulators 140 to generally mimic the motion of standard laparoscopic surgical tools. In addition to allowing rotation about the approximated axes located generally at about the same location as the shoulder joints 148, offset planar hinge joints 144 also allow for each manipulator 140A, 140B to rotate about its respective axis and translate through horizontal leaves 158.

In some alternative embodiments, the approximated axis of rotation of the manipulators 140 with respect to console 142 is adjustable to account for variable skin thicknesses. This is accomplished by moving the offset planar hinge joints 144 vertically or translationally away from console 142 or adjusting the angle of the fixed pins 162. Those skilled in the art will recognize and appreciate that this adjustment can also be in the form of an electronic setting which can be calibrated for various thicknesses of the abdominal wall depending on the individual patient.

Although many of the figures in this application depict console as having two manipulators, it is understood that the console may include any number of manipulators. For example, the console may include two or more sets of manipulators with each set dedicated to a different robotic device being used cooperatively within a body cavity of the patient. Alternatively, the console or the manipulators may be capable of operating more than one robotic device. For example, in one embodiment, the manipulators or the console is provided with a switch or any other type of known input that allows the user to switch communications from one robotic device to another, thereby switching operating control from one robotic device to another. This switch may be a mechanical toggle-type switch on the console, or a footpedal on the floor. The switch could also be integrated into a touchscreen on the console with the switching capability implemented in software and activated by pressing a graphic on the console touchscreen interface. Thus, the console and the manipulators may be used with one robotic device, two robotic devices, or any number or combination of robotic devices that might be used together for a surgical procedure. In addition, the console and the manipulators may be used to control not only the robotic devices within the patient's body cavity, but also the robotic devices that are not disposed entirely within the body cavity.

In an alternative embodiment, the console may not include any manipulators. In embodiments in which the console does not include any manipulators, a console magnet may be used to move the robotic device around within the body cavity. In a further embodiment, the manipulators and the console may be physically separate components.

Figure 8A:
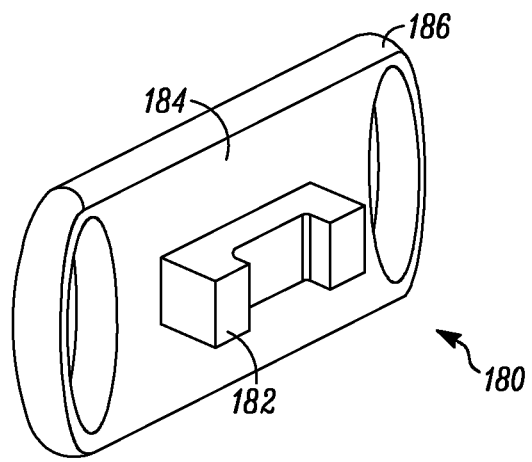
FIG. 8A is a rear perspective view of a console of the surgical visualization and device manipulation system, according to one embodiment.
Figure 8B:
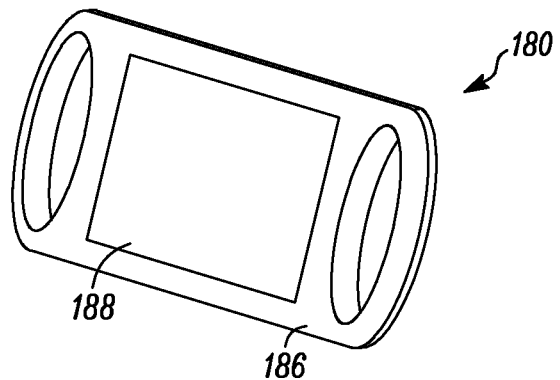
FIG. 8B is a front perspective view of the console of the surgical visualization and device manipulation system, according to the embodiment of FIG. 8A.

FIGS. 8A and 8B show an embodiment of a console 180 without manipulators. In this embodiment, console magnet 182 is attached to a rear face 184 of console 186. Alternatively, as with any console disclosed herein, console magnet 182 may be two or more magnets positioned in any configuration or location on console 186 so as to be able to be magnetically coupled with a robotic device. In practice, console 186 is positioned on or adjacent to an external surface of body cavity such that rear face 184 and console magnet 182 of console 186 are adjacent to the external surface. In this position, console magnet 182 can interact with any robotic device disposed within the patient's body and in certain embodiments can maintain the device in a position against internal cavity wall of the body cavity.

In one embodiment, the console 186 of FIGS. 8A and 8B is used to operate a robotic device that has no arms. That is, the console 186 can be used to move a robotic device from one point to another within the patient's body by moving the console 186 outside the body, and further can have actuation components other than arms to operate the various kinds of robotic devices that may be positioned inside the patient. Without being limiting, examples of the types of robotic devices that could be operated with the console 186 include robotic camera devices such as those disclosed in 11/766, 683. In this embodiment, visual feedback from a robotic camera can be displayed on the video screen 188. In further embodiments, the console 186 has non-arm controls such as buttons or other types of actuators that allow the console 186 to be used with any robotic device.

Figure 9:
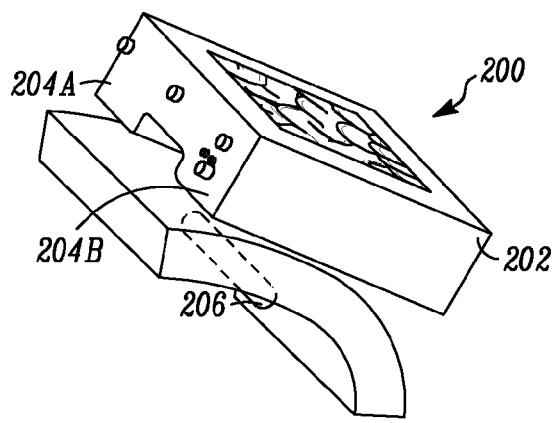
FIG. 9 is a side perspective view of a surgical visualization and device manipulation system positioned relative to a body cavity of the patient, according to an alternative embodiment.
Figure 10A:
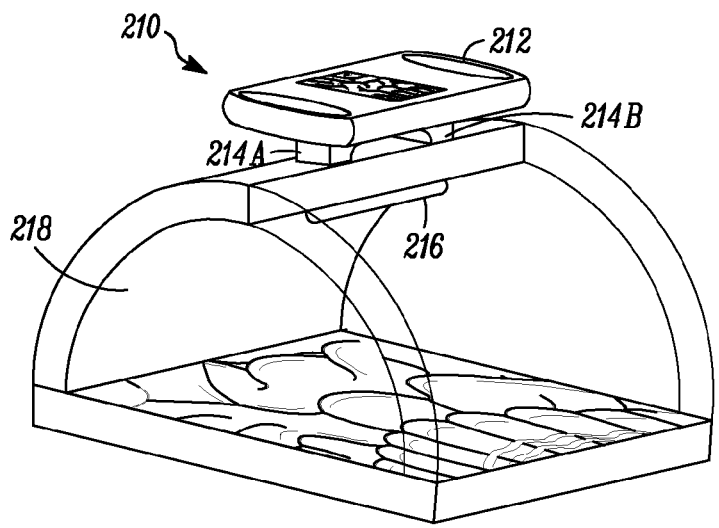
FIG. 10A is a perspective view of a surgical visualization and device manipulation system positioned relative to a body cavity of the patient, according to an alternative embodiment.
Figure 10B:
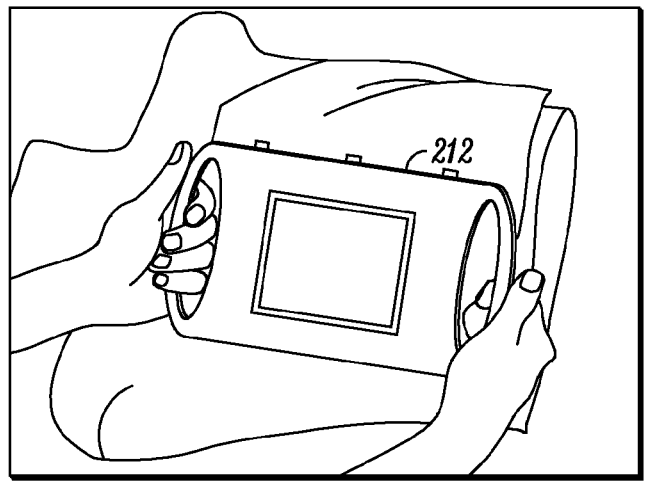
FIG. 10B is a perspective view of a surgical visualization and device manipulation system positioned relative to a body cavity of the patient, according to an alternative embodiment.

Two further embodiments of consoles without manipulator arms are provided in FIGS. 9, 10A, and 10B. FIG. 9 shows a surgical visualization and device manipulation system 200 having console 202, console magnets 204A and 204B (collectively referred to as "console magnets 204") and magnetically-controlled robotic device 206. FIGS. 10A and 10B shows a surgical visualization and device manipulation system 210 having console 212, first console magnet 214A and second console magnet 214B (collectively referred to as "console magnets 214") and magnetically-controlled robotic device 216. Given that the consoles 202, 212 have no manipulators, the robotic devices 206 and 216 are thus controlled by movement of consoles 202 and 212 and console magnets 204 and 214, respectively, over body cavity 218.

It is understood that any console embodiment disclosed herein can be used to position and/or control any known robotic device that can be used for medical procedures.

Figure 11:
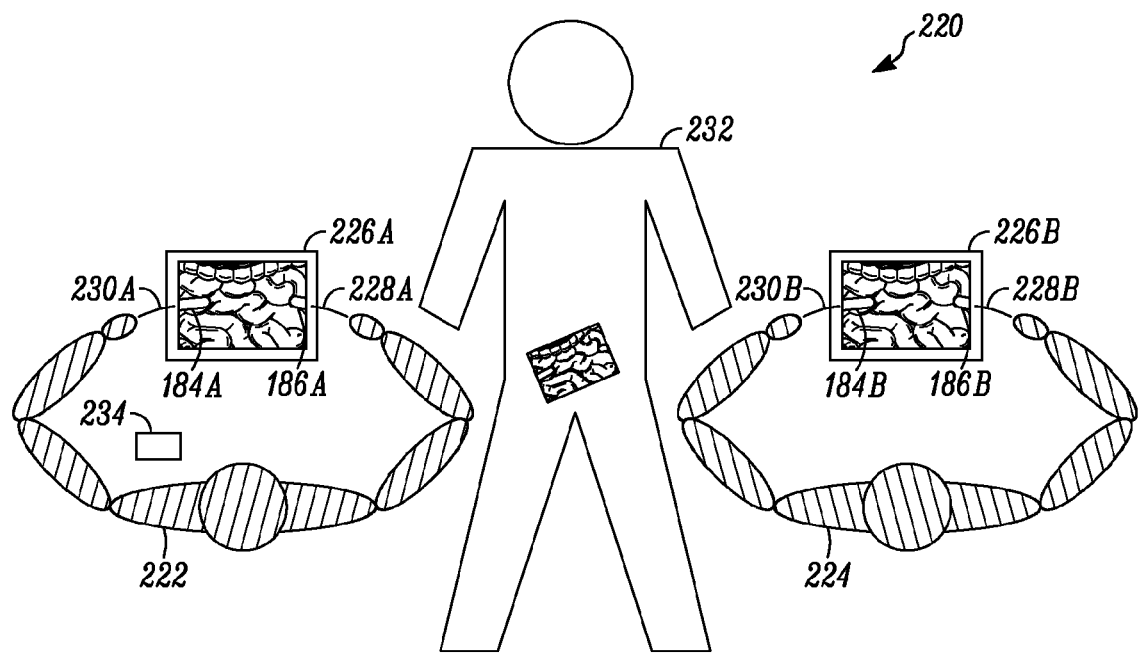
FIG. 11 is a schematic representation of a surgical visualization and device manipulation system, according to another embodiment.

FIG. 11 depicts a surgical system 220 according to one embodiment in which the system includes two consoles: one for the instructor 222 and another for the student 224. The two consoles 226A, 226B are connected or otherwise coupled to a robotic device (not shown) positioned within the patient's body. Each console 226A, 226B has a right manipulator arm 228A, 228B and a left manipulator arm 230A, 230B. Alternatively, each console 226A, 226B can have one manipulator arm, no manipulator arms, or any other configuration as described herein with respect to the various console embodiments. In this embodiment, the commands provided at the student console 226B can be bypassed for various purposes such as preventing the end effectors from damaging tissues.

As shown in FIG. 11, the two consoles 226A, 226B are connected to the in vivo surgical robot used inside the patient. The connection between each of the consoles 226 and the robotic device (not shown) can be any connection as described herein. It is understood that the consoles 226 can be positioned anywhere. In one embodiment, the consoles 226 are positioned directly on the patient 232. Alternatively, they can be positioned beside the patient 232. For example, in one embodiment in which they are positioned beside the patient 232, both consoles 226A, 226B are placed on stands similar to music stands. It is further understood that when the consoles 226 are positioned beside or in the same room with the patient 232, the consoles 226A, 226B can be positioned such that the users 222, 224 at the consoles 226A, 226B are facing the patient 232. In one embodiment, the consoles 226A, 226B can be positioned side by side. Alternatively, the consoles 226A, 226B can be positioned in any orientation in the room with the patient 232.

In accordance with one implementation as discussed above, both consoles 226 are positioned in the same room as the patient. Alternatively, one console is positioned in the same room as the patient and the other console is positioned somewhere else such as another room in the same building or elsewhere in the same country or elsewhere in the world. In a further alternative, both consoles 226A, 226B are positioned elsewhere outside the room containing the patient 232. As a result, the surgeon 222 and/or the student 224 can operate a console remotely, including from a different location in the world.

One embodiment of the system depicted in FIG. 11 enhances patient safety. That is, the system makes it possible for multiple hands or multiple operators to have access to the instruments at the same time while also allowing the instructor 222 to disconnect (or "freeze") the student's console 226B from the robotic device (that is, disconnect the communication between the student's console 226B and the robotic device such that commands cannot be sent from the student's console 226B) by the touch of a pedal 234 or button (not shown). In this way, the instructor 222 can take over control of the robotic device during surgery if/when necessary.

In accordance with another implementation, the console manipulators 228, 230 (also referred to as "manipulator handles," "handles," or "joysticks") not only have position encoders (used to determine the joystick positions) connected to them as described with other console embodiments discussed above, but the consoles 226A, 226B can also have actuators (not shown) configured to drive the handles 230, 228. That is, the actuators are coupled to the handles 230A, 228A such that the actuators can be actuated to move the handles 230B, 228B. According to one embodiment, the actuators on the second console 226B can be coupled with the first console 226A such that manipulation of the handles at the first console 226A can cause the actuators at the second console 226B to actuate the handles 228B, 230B. Thus, one implementation provides for a master-slave relationship between the two consoles 226A, 226B. It is understood that this master-slave relationship could operate in either direction, so that either the manipulators 230A, 228A at the first console 226A are controlling the manipulators 230B, 228B at the second console 226B or vice versa.

According to one embodiment, the master-slave connection implementation described above with respect to the consoles 226 can allow the student to observe the instructor's motions during surgery. That is, the movement of the handles 230A, 228A at the instructor's console 226A causes the handles 230B, 228B at the student's console 226B to move in the same way, thereby allowing the student 224 to observe the movements of the handles 230B, 228B. Similarly, when the student 224 takes control, the instructor's console 226A can become the slave console. That is, the handles 230B, 228B of the student's console 226B can be coupled to the handles 230A, 228A of the instructor's console 226A such that movement of the student console handles 230B, 228B actuates similar movement of the instructor's console handles 230A, 228A so that the instructor 222 can observe or maintain a "feel" for what the student 224 is doing. In accordance with one alternative embodiment, the instructor's console 226A can also have a pedal 234, button, or any other kind of component (not shown) as also discussed above for disconnecting the student console 226B from the end effectors 184, 186 or otherwise disruption communications between the student console 226B and the in vivo device (not shown). Thus, the instructor 222 can observe the student's 224 actions via the master-slave connection between the consoles 226A, 226B and, if necessary, actuate the disconnection pedal 234 to easily take over the surgery.

It is understood that the linked consoles as described above could include any number of consoles with a central command for controlling which console has control over the in vivo surgical robotic device. In accordance with another implementation, commands from multiple consoles can be used together to command the robotic device. In this embodiment, the multiple commands can be scaled to allow the instructor to slowly allow more control for the student.

Figure 12A:
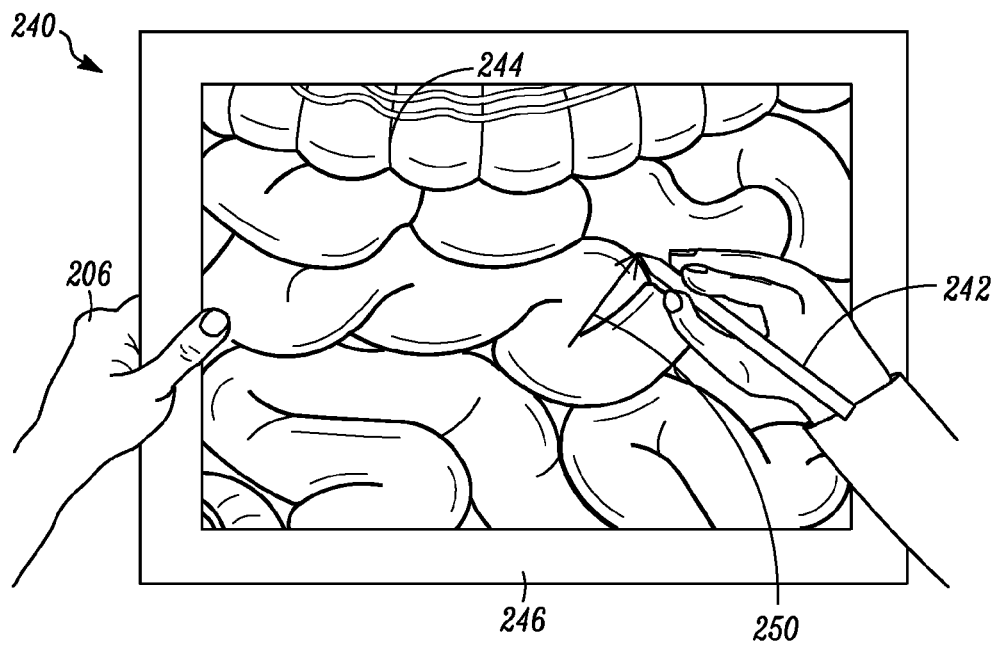
FIG. 12A is a schematic representation of an instructor console of the surgical visualization and device manipulation system, according to a further embodiment.
Figure 12B:
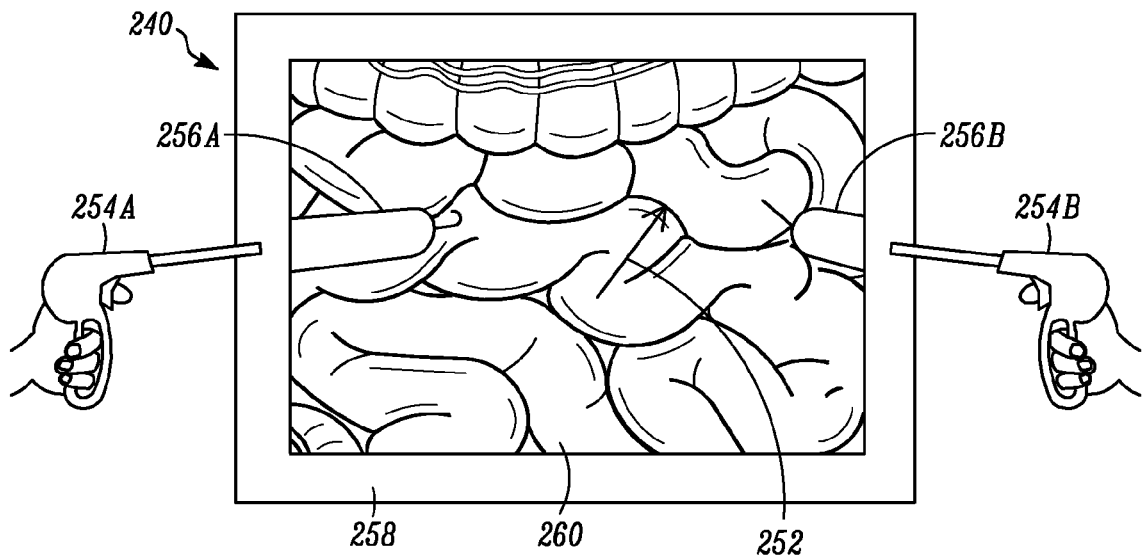
FIG. 12B is a schematic representation of a student console of the surgical visualization and device manipulation system, according to the embodiment of FIG. 12A.

FIGS. 12A and 12B depict a surgical system 240 according to another embodiment in which the instructor console depicted in FIG. 12A is configured to allow the user to touch a pen 242 (or any pen-like instrument or even the user's finger) on the screen 244 to provide information and/or instructions that appear on the student console 258, shown in FIG. 12B. The instructor console 246 can also be referred to as the "first console" or "primary console,", while the student console 258 can also be referred to as the "second console" or "secondary console." In this implementation, the system 240 is configured such that the instructions drawn on the screen 244 in FIG. 12A appear on the student's screen 260 in FIG. 12B. In one embodiment, the instructor 248 can use this system 240 to easily communicate with the student 262. For example, the instructor 248 could easily illustrate important surgical features and point to sites of interest.

It is understood that that the user 206 of the primary console 246 need not be an instructor, but rather can be any user who can or wants to enter information at the primary console 246 such that it appears on the secondary console 258. It is also understood that, according to one alternative implementation, the entry of information on one screen and appearance on the other screen can operate in either direction, so that information entered on either screen appears on the other.

It is also understood that the technology discussed above with respect to FIGS. 12A and 12B can be used with standard laparoscopic surgery using standard tools or it can be combined with the use of in vivo robotic devices as shown in FIG. 12B.

When used with standard laparoscopic technology, according to one embodiment, the surgeon 206 provides the information using the pen-like instrument 242 on a touch screen monitor 244 that may or may not include the video feed from the laparoscope. This input is then overlaid onto or otherwise appears on the monitor or screen 260 the surgical team is using. In this embodiment, the input touch screen 244 further allows the instructor 206 to erase any markings or clear the screen 244. Furthermore, the system 240 also allows segments of the procedure (or the entire procedure) to be saved. These segments could include video, audio, and instructions drawn on the screen 244. This allows the instructor 206 or student 262 to review the surgery or even replay the surgery using either console 246, 258 in slave mode.

In one embodiment, the touch screen 244 used in the above systems is a Touchscreen tablet notebook such as the Pavilion TX1000Z by Hewlett Packard located in Palo Alto, Calif. In an alternative embodiment, the touchscreen is a Touchscreen overlay such as the MagicTouch touchscreen by Mass Multimedia, Inc., located in Colorado Springs, Colo. In one embodiment, the communication between screens is transferred via USB technology, while in another embodiment the student screen 260 is a second screen operating from the instructor tablet notebook using a standard 9-pin monitor output. In a further alternative, the touch screens utilized in the various embodiments of the above system can be any known touch screen known in the art.

Figure 13:
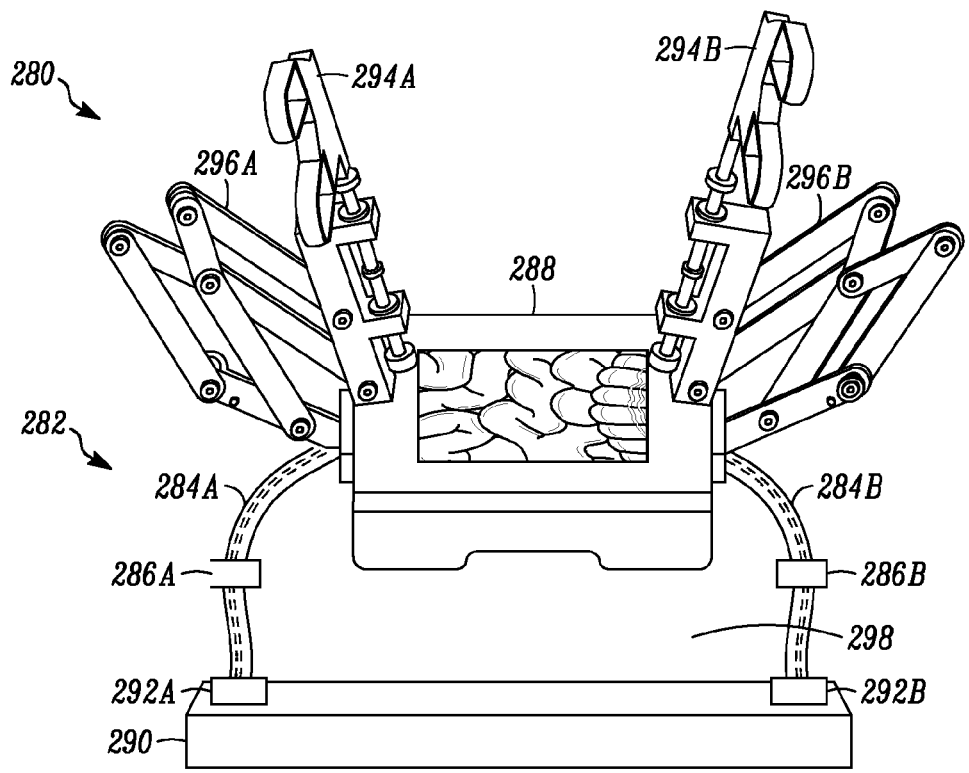
FIG. 13 is a perspective view of a surgical visualization and device manipulation system having a stabilization system, according to another embodiment.

FIG. 13 depicts a further embodiment of a surgical system 280 having a stabilization system 282. The stabilization system 282, according to one embodiment, allows the console 288 to be stabilized and/or fixed in place. Such a stabilization system 282 can reduce instability of the surgical environment caused by the weight of the console 288 and manipulators 294 and/or the force applied by the surgeon during use that can result in rocking and movement of the console 288 and handles 294 in relation to the patient's body and/or the device 298 disposed within the patient's body.

As shown in FIG. 13, the system has two linkages 284. One end of each linkage 284 is attached to the console 288, and the other end of each linkage 284 is attached to a base 290. Alternatively, the linkages 284 can be attached to the manipulator arms 294 or any other portion of the visualization and control system 280.

The base 290, according to one embodiment, is a platform, table (including, for example, an operating table), gurney, stand, or a cart. Alternatively, the base 290 is a translating component that is coupled to and configured to translate along the operating table or other similar object in a treatment area, such that the stabilization system 282 can move back and forth next to or along the side of the patient.

In a further alternative, the base 290 is the floor or any other stable object. The attachment via the linkages 284 of the console 288 to the base 290 provides stability to the component 288. In yet another alternative, there is no base and the linkages 284 are attached or coupled to the patient in some fashion. For example, in one embodiment, the linkages 284 can be attached to a strap or other object around the patient's leg or waist or any other type of object that is attached or coupled to the patient.

In one aspect, the linkages 284 further provide the surgeon with the ability to grossly position the robot 298 inside the patient's body and then lock the system 282 into an appropriate or desired position for the procedure. In one implementation, the base 290 provides absolute rigidity, or alternatively it provides various amounts of damping to the movement of the system 282. Further, the system 282 can be subsequently unlocked to allow the surgeon to reposition during the procedure or remove the system 282.

The linkages 284 can be any structures capable of attaching and stabilizing the system 280 and the base 290. In one alternative embodiment, the linkages 284 have clamps (shown schematically as 292) that assist with attachment to the base 290.

In another embodiment, the linkages 284 further have one or more joints (shown schematically as 286) that allow the linkages 284 to be reconfigured or repositioned as needed. Such joints 286 can be lockable such that they can be positioned and then fixed into place. Further, the joints 286 can also provide for variable amounts of damping.

According to one embodiment as shown in FIG. 13, the stabilization system 282 has two linkages 284. Alternatively, the system can have one linkage or more than two linkages. The number of linkages can vary depending on the patient's size, the procedure being performed, and/or the specific procedural equipment (including the specific robotic devices) being used.

The mechanical joints, linkages, and attachment clamps of system 282 can be manufactured from metal or polymers or any other known material used in medical devices. Further, the linkages 284 can be rigid or deformable. In embodiments in which the linkages 284 are deformable, the joints 286 can be adjusted for gross positioning while fine positioning is attained by deforming or bending the linkages to allow for precise position of the visualization and control system.

Any robotic device configured for use within a patient's body cavity may be used with one or more of the various surgical visualization and device manipulation systems described herein. As used herein, "robotic devices" is intended to mean any device that may be used laparoscopically or endoscopically during a surgical procedure. Some of the various robotic devices that may be used with the systems disclosed herein include, but are not limited to, any one or more of the devices disclosed in copending U.S. patent application Ser. No. 11/932,441 (filed on Oct. 31, 2007 and entitled "Robot for Surgical Applications"), Ser. No. 11/695,944 (filed on Apr. 3, 2007 and entitled "Robot for Surgical Applications"), Ser. No. 11/947,097 (filed on Nov. 27, 2007 and entitled "Robotic Devices with Agent Delivery Components and Related Methods), Ser. No. 11/932,516 (filed on Oct. 31, 2007 and entitled "Robot for Surgical Applications"), Ser. No. 11/766,683 (filed on Jun. 21, 2007 and entitled "Magnetically Coupleable Robotic Devices and Related Methods") and Ser. No. 11/766,720 (filed on Jun. 21, 2007 and entitled "Magnetically Coupleable Surgical Robotic Devices and Related Methods"), 60/890,691 (filed on Feb. 20, 2007), 60/949,391 (filed Jul.

12, 2007), 60/949,390 (filed Jul. 12, 2007), 60/956,032 (filed Aug. 15, 2007), 60/983,445 (filed Oct. 29, 2007), 60/990,062 (filed Nov. 26, 2007), 60/990,076 (filed Nov. 26, 2007), 60/990,086 (filed Nov. 26, 2007), 60/990,106 (filed Nov. 26, 2007), and 60/990,470 (filed Nov. 27, 2007), all of which are hereby incorporated herein by reference in their entireties.

In an exemplary embodiment, the robotic device can be a natural orifice translumenal endoscopic surgical device, such as a NOTES device. Those skilled in the art will appreciate and understand that various combinations of features are available including the features disclosed herein together with features known in the art.

Figure 14A:
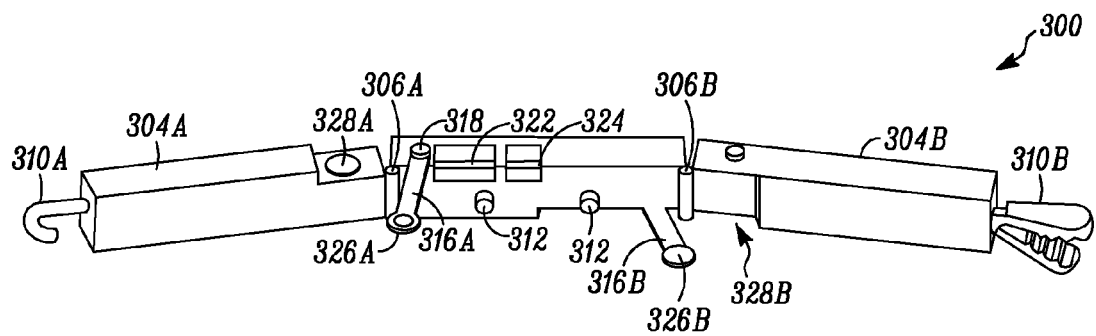
FIG. 14A is a perspective view of a robotic device of the surgical visualization and device manipulation system in an unfolded position, according to one embodiment.
Figure 14B:
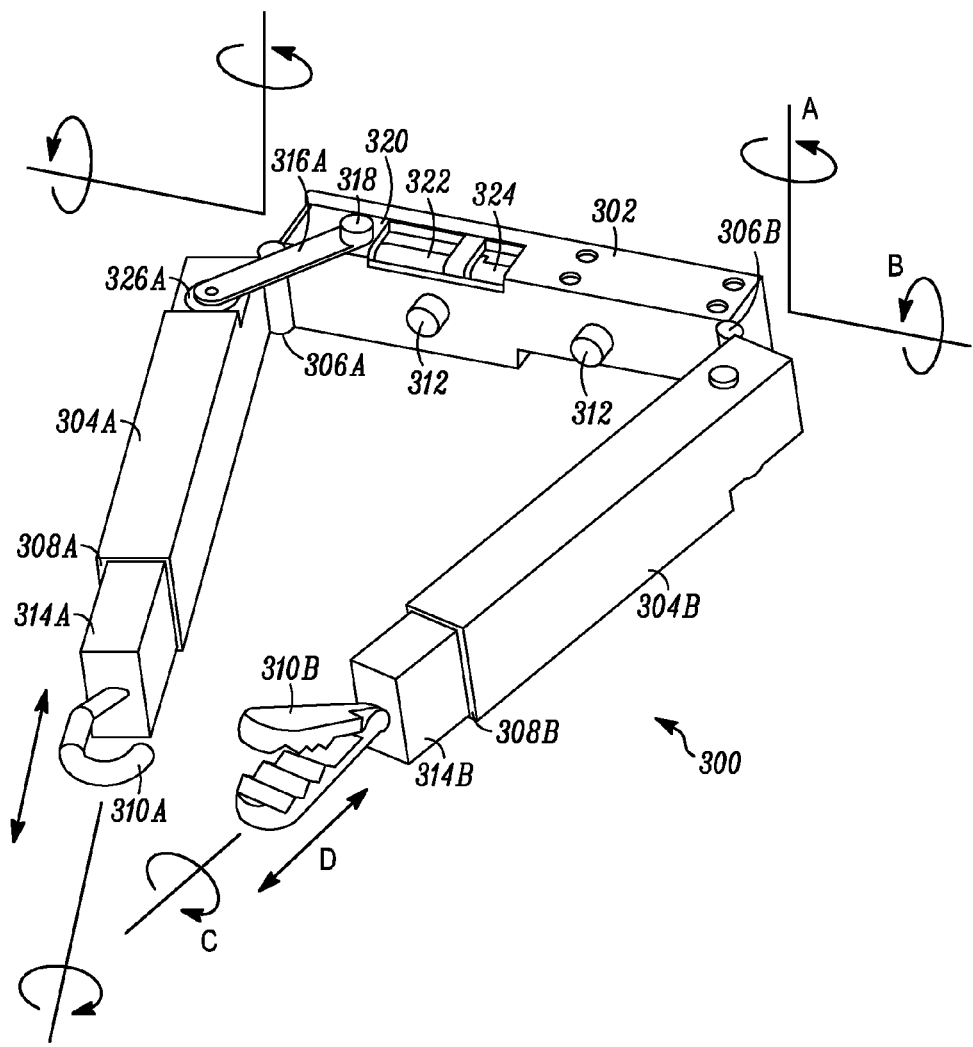
FIG. 14B is a diagram of the rotational axes of the robotic device of the surgical visualization and device manipulation system in a folded position, according to the embodiment of FIG. 14A.

FIGS. 14A and 14B show one embodiment of robotic device 300 for use with one or more of the systems disclosed herein, in an unfolded position and a folded position, respectively. FIGS. 14A and 14B will be discussed in conjunction with one another. Robotic device 300 includes device magnet (not shown), body 302, first arm 304A and second arm 304B (collectively referred to as "arms 304"), first shoulder joint 306A and second shoulder joint 306B (collectively referred to as "shoulder joints 306"), first elbow joint 308A and second elbow joint 308B (collectively referred to as "elbow joints 308"), first end effector 310A and second end effector 310B (collectively referred to as "end effectors 310") and imaging component 312. Here the shoulder joints 306 are rotatable in two directions, the elbow joints 308 are translational in one direction, and the end effectors 310 are rotational in one direction. In one embodiment, device magnet (not shown) can interact with an external magnet such as a console magnet to position the robotic device 300 within a patient and in spatial relation to the console in similar fashion to the implementations discussed above.

The upper (or "first") portion of first arm 304A is pivotally connected to body 302 by first shoulder joint 306A. Further, the lower (or "second") portion 314A of the first arm is translationally coupled to the upper portion 304A at the first elbow joint 308A. First end effector (or "operational component") 310A is rotationally attached to the lower portion 314A. Likewise, the upper portion of second arm 304B is pivotally connected to body 302 by second shoulder joint 306B, while the lower portion 314B is translationally coupled to the upper portion 304B at the second elbow joint 308B. Second end effector 310B is rotationally attached to the lower portion 314B. The connections of arms 304 to body 302 allow arms 304 to rotate about an axis perpendicular to the length of body 302 and further about an axis parallel to the length of the body 302.

In accordance with one embodiment as best shown in FIG. 14B, each arm 304 has 4 degrees of freedom (DOF) so that the motion of end-effectors 310 is similar to the motion of standard laparoscopic tools (three rotations and one translation). Each arm 304 can rotate around an axis perpendicular to the length of the body 302 as shown by arrow A (wherein the rotation is also referred to as "yaw"), and further can rotate around an axis parallel to the body 302 as shown by arrow B (wherein the rotation is also referred to as "pitch"). In addition, each arm 304 can rotate at the end effectors 310 around an axis parallel to the arm 304 as shown by arrow C (wherein the rotation is also referred to as "roll"). Finally, each arm 304 can also be extended translationally by the extension of the lower portions 314 as shown by arrow D to lengthen the reach of the end effectors. In this embodiment, the lengthening or translation D is accomplished using a prismatic joint which is referred to here as the elbow joint. Using robotic device 300 with arms 304 having the same degrees of freedom as standard laparoscopic tools in conjunction with a console having manipulators according to various embodiments disclosed herein allows the user to operate the manipulators in a manner that substantially replicates the movement of standard, non-robotic laparoscopic tools. While various specific robotic devices may be shown herein, it is to be appreciated that numerous robotic devices with arms or end effectors having various degrees of freedom are available. In a further embodiment, it is understood that the consoles disclosed herein can also be used with various robotic devices having no arms or end effectors.

Lower portions 314 of arms 304 are fitted with end effectors 310 that are extendable and retractable from upper arm portions 304. The design of end effectors 310 are based on existing standard hand-held laparoscopic tools. As used herein, "end effector" is intended to mean any component that performs some action or procedure related to a surgical or exploratory procedure, and in particular any device that can perform, or assist in the performance of, any known surgical or exploratory laparoscopic procedure. An end effector can also be referred to as an "operational component". In one aspect, the one or more end effectors 310 assist with procedures requiring high dexterity. In currently known standard techniques, movement is restricted because passing the rigid laparoscopic tool through a small incision restricts movement and positioning of the tool tip. In contrast, a robotic device having an operational component inside a body cavity is not subject to the same constraints. Examples of end effectors 310 include, but are not limited to: clamps, scalpels, any type of biopsy tool, graspers, forceps, staplers, cutting devices, cauterizing devices, suction/irrigation devices, ultrasonic burning devices or other similar component. It is understood that the end effector can be any end effector, including interchangeable end effectors, as disclosed in any of the patents or applications disclosed herein or any other known end effector used in robotic devices for medical procedures. In addition, it is understood that these devices can also include any additional components useful in operating the end effectors, such as actuators, as known in the art and/or described in the incorporated patents or applications.

Robotic device 300 can provide two dimensional visual feedback, three dimensional visual feedback or stereoscopic imaging to a surgeon via imaging component 312. According to one embodiment, imaging component 312 (also referred to herein as a "camera") is disposed on a center portion of body 302 of robotic device 300. It is understood that imaging component 312 as used herein is intended to mean any device for capturing an image. Imaging component 312 provides visual feedback of body cavity to a visual display on a console (such as, for example, the console 12 of FIG. 1). Various embodiments of imaging component 312 include, but are not limited to: a camera providing real-time video to the user through visual display, a stereo camera that creates a three-dimensional image, a complementary metal oxide semiconductor ("CMOS") digital image sensor, a square 7 mm camera, any small camera similar to those currently used in cellular or mobile phones, any imaging device currently used in or with endoscopic devices, a pan-and-tilt camera, and any device that provides a sufficient depth of field to observe the entire abdominal cavity. An exemplary embodiment of a complementary metal oxide semiconductor ("CMOS") digital image sensor is Model No. MT9V125 from Micron Technology, Inc., located in Boise, Id. Further, any imaging component disclosed in any of the patents or applications incorporated herein can be incorporated into any device used with systems and devices discussed herein. Although FIGS. 14A and 14B depict imaging component 312 disposed on the center portion of body 302 of robotic device 300, imaging component 312 may be disposed on any portion of body 302 or robotic device 300.

Imaging component 312, in one implementation, can also include a light component (not shown) configured to light the area to be viewed, also referred to as the "field of view." Light component can be positioned proximate to any imaging component and end effectors to provide constant or variable illumination for the imaging component so that the view of the area of interest (such as, for example, the surgical site) is improved or the viewing area is increased. Light component illuminates the field of view of the surgical site, thereby facilitating operation of any robotic device and/or any other devices being used in conjunction with such robotic device. In one example, lighting component is a light emitting diode (LED) light. In another example the lighting component can be a fiber optic filament or cable with light source outside of the patient and transmitted to the robot via a fiber optic cable. In a further alternative, lighting component can be any suitable illumination source, including any such source as disclosed in any of the patents or applications incorporated herein. Although imaging component 312 is discussed as including only one light component, imaging component 312 may include any number of light components. In an exemplary embodiment, the light component may include two 5 mm LEDs.

Robotic device 300 can be inserted into or positioned in a body cavity in many ways, including the use of a standard laparoscopic port or a natural orifice approach or any other method known in the art or disclosed in any of the patents or applications incorporated herein. In one embodiment, arms 304 of robotic device 300 are partially disconnected by disconnecting magnets 326A and 326B from magnets 328A and 328B, respectively, at each of shoulder joints 306A and 306B. This increases the level of rotation of arms 304 and allows robotic device 300 to take a linear but flexible structure so that it can be more easily inserted into body cavity. Robotic device 300 can then be assembled once inside the body cavity. This assembly involves attaching magnet 328A to 326A and magnet 328B to 326B. In one example the surgeon can actively perform this assembly using other tools. In another example the arms are spring loaded to move to this position after insertion.

It is understood that the robotic device 260 depicted in FIGS. 14A and 14B contains various motors and other internal components for operation of the device similar to those disclosed in U.S. application Ser. No. 11/766,683, entitled "Magnetically Coupleable Robotic Devices and Related Methods," filed on Jun. 21, 2007, which is incorporated by reference above. It is also understood that this device is merely exemplary of the many robotic devices that can be used with the visualization and control systems disclosed herein.

While multiple embodiments are disclosed, still other embodiments will become apparent to those skilled in the art from the following detailed description, which shows and describes illustrative embodiments. As will be realized, the embodiments are capable of modifications in various obvious aspects, all without departing from the spirit and scope of the invention. Accordingly, the drawings and detailed description are to be regarded as illustrative in nature and not restrictive.

EXAMPLE 1

The following is an exemplary kinematic design of the motion of one embodiment of a NOTES robotic device that can be used with any console as disclosed herein. The design is merely exemplary of one particular embodiment of a robotic device and is not intended to be limiting in any fashion, as any number of robotic devices can be used in conjunction with a console, as discussed above.

Figure 15A:
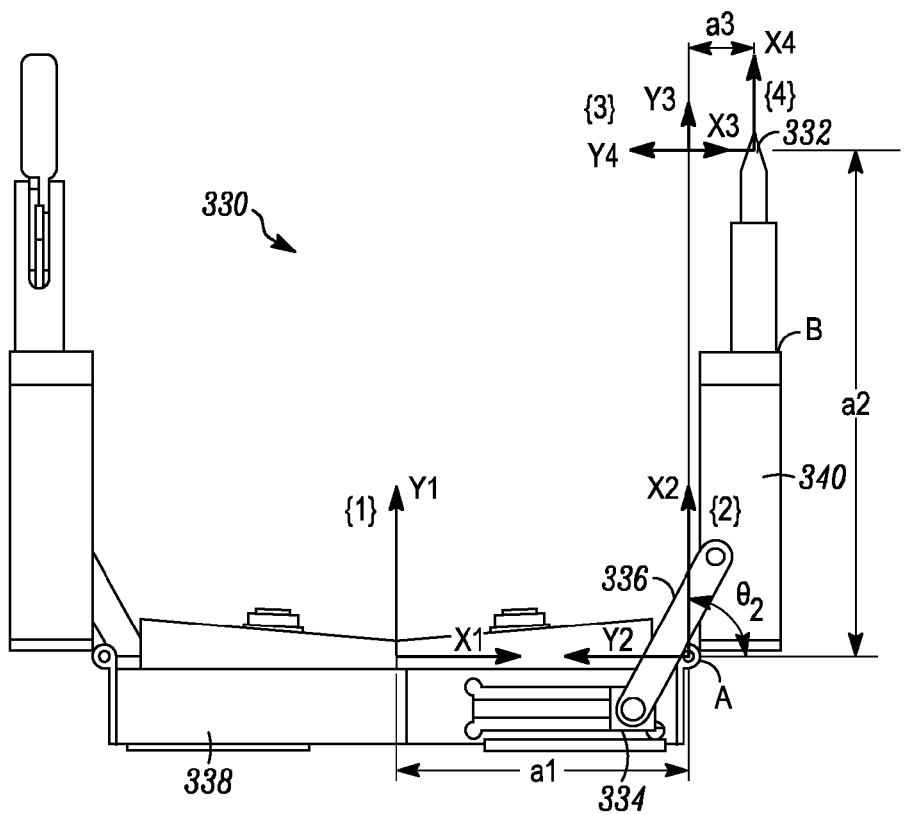
FIG. 15A is a diagram of a kinematic model of a robotic device of the surgical visualization and device manipulation system, according to one embodiment.

This particular design begins with a kinematic model of the robotic device, as shown in FIG. 15A. Here the kinematic model of the NOTES robot is shown overlaid on the robot schematic in FIG. 15A. The robot is a 2-DOF planar manipulator with a rotational shoulder joint A and prismatic arm B denoted by joint variables $\theta_2$ and $a_2$ respectively.

The Denavit-Hartenberg parameters for the robot are shown in Table 1. The parameter $\alpha_0$ defines the angle of rotation of the robot with respect to a universal frame {0} that is used to introduce gravity. Parameters $a_1$ and $a_3$ are constants defining the body width and offset of the end-effector with respect to the axis of rotation of the shoulder joint, respectively.

TABLE 1

| DENAVIT-HARTENBERG PARAMETERS | | | | |
|---|---|---|---|---|
| i | $\alpha_{i-1}$ | $a_{i-1}$ | $\theta_i$ | di |
| 1 | $\alpha_0$ | 0 | 0 | 0 |
| 2 | 0 | $a_1$ | $\theta_2$ | 0 |
| 3 | 0 | $a_2$ | −90 | 0 |
| 4 | 0 | $a_3$ | 90 | 0 |

Using the general kinematic model and the Denavit-Hartenberg parameters, the equations that describe the location [x, y] of the end-effector 332 with respect to frame {1} are defined in Equation 1 and used to derive the Jacobian of the robot as given in Equations 2 and 3. The position of the end effectors 332 with respect to frame {1} is denoted as $^1P_{Org4}$.

$$^1P_{Org4} = \begin{bmatrix} c_{\theta_2} a_2 + s_{\theta_2} a_3 + a_1 \\ s_{\theta_2} a_2 - c_{\theta_2} a_3 \end{bmatrix} = \begin{bmatrix} x \\ y \end{bmatrix} \quad \begin{array}{l} s_i = \sin(i) \\ c_i = \cos(i) \end{array} \quad \text{Equation 1}$$

$$J(q_1, q_2) = J(\theta_2, a_2) = \frac{\partial}{\partial q_i} {}^1P_{Org4} \quad \text{Equation 2}$$

$$^1J = \begin{bmatrix} -s_{\theta_1} a_2 + c_{\theta_2} a_3 & c_{\theta_1} \\ c_{\theta_1} a_2 + s_{\theta_2} a_3 & s_{\theta_1} \end{bmatrix} \quad \text{Equation 3}$$

Inverse kinematic equations for joint variables $a_2$ and $\theta_2$ are obtained by solving (1). Equation 4 lists the inverse kinematic equation that describes variable $a_2$, while Equation 5 lists $\theta_2$.

$$a_2 = \sqrt{x^2 + y^2 - 2xa_1 + a_1^2 - a_3^2} \quad \text{Equation 4}$$

$$\theta_2 = \arctan2\left(\frac{xa_3 + ya_2 - a_1 a_3}{x^2 + y^2 - 2xa_1 + a_1^2}, \frac{a_2(x - a_1) - ya_3}{x^2 + y^2 - 2xa_1 + a_1^2}\right) \quad \text{Equation 5}$$

Figure 15B:
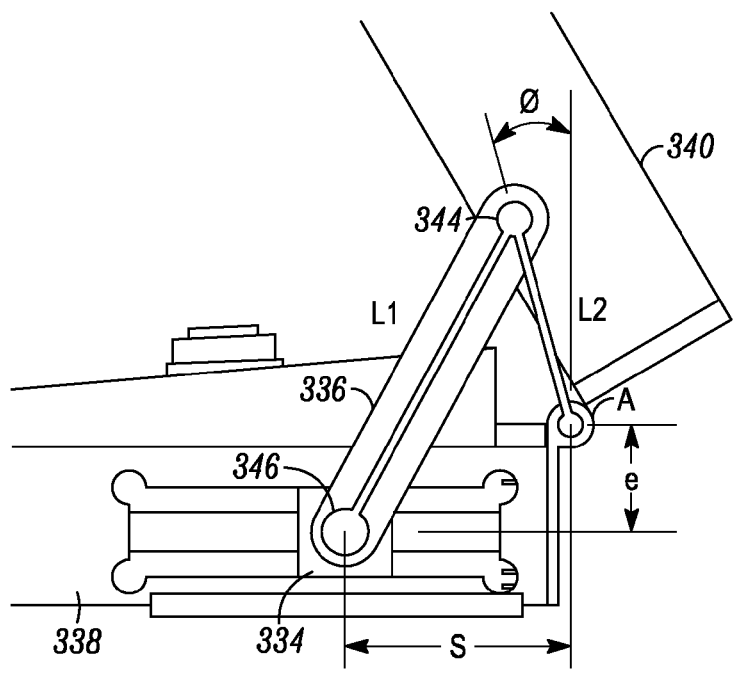
FIG. 15B is a close-up diagram of the shoulder joint of a kinematic model of a robotic device of the surgical visualization and device manipulation system, according to the embodiment of FIG. 15A.

The geometry of the shoulder joint is given by the kinematic model of an offset slider crank mechanism, shown in FIG. 15B. Distance, e, is the offset distance from the line of action of the slider 334 to the axis of rotation A of the arm 340 with respect to the main body 338, and distance, s, is the location of the slider 334 with respect to the axis of rotation A. The distance L1 is the length of the linkage 336 between pins 344 and 346. The distance L2 is the length between axis of rotation A and the pin 344. Position and velocity equations derived from the above configuration can be solved for slider position and velocity as functions of crank position, $\phi$, and angular velocity $\dot{\phi}$. Equation 6 describes the slider position s, while Equation 7 describes the slider velocity $\dot{s}$.

$$s = L_2 \sin\varphi + L_1 \sqrt{1 - \left(\frac{e + L_2 \cos\varphi}{L_1}\right)^2} \quad \text{Equation 6}$$

$$\dot{s} = \dot{\varphi}\left[L_2 \cos\varphi + \frac{L_2 \sin\varphi}{L_1} \frac{(e + L_2 \cos\varphi)}{\sqrt{1 - \left(\frac{e + L_2 \cos\varphi}{L_1}\right)^2}}\right] \quad \text{Equation 7}$$

Open-loop control tests were performed with the NOTES robot for a Cartesian straight line path. Using a linear function with parabolic blends and assuming a maximum allowable velocity, a path was planned in Cartesian space. The Cartesian path was converted to joint space using the inverse kinematic relationships, and the inverse of the Jacobian, all described above in Equations 1 through 7.

Figure 15C:
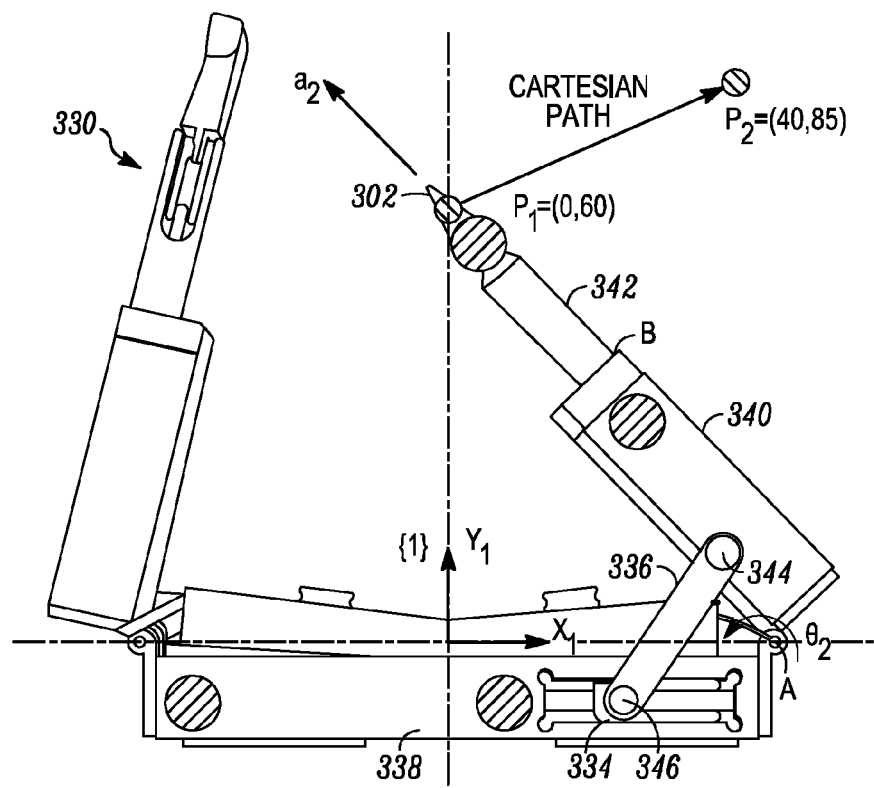
FIG. 15C is a diagram of an actuation path of a robotic device of the surgical visualization and device manipulation system, according to the embodiment of FIG. 15A.

A path from P1=(0,60) to P2=(40,85) (mm) in Cartesian space was generated, as shown in FIG. 15C. Joint variable $\theta_2$ was then converted to actuator space, where velocity was linearly related to motor speed, using the equations derived for the offset slider-crank mechanism (Equations 6 and 7).

Figure 15D:
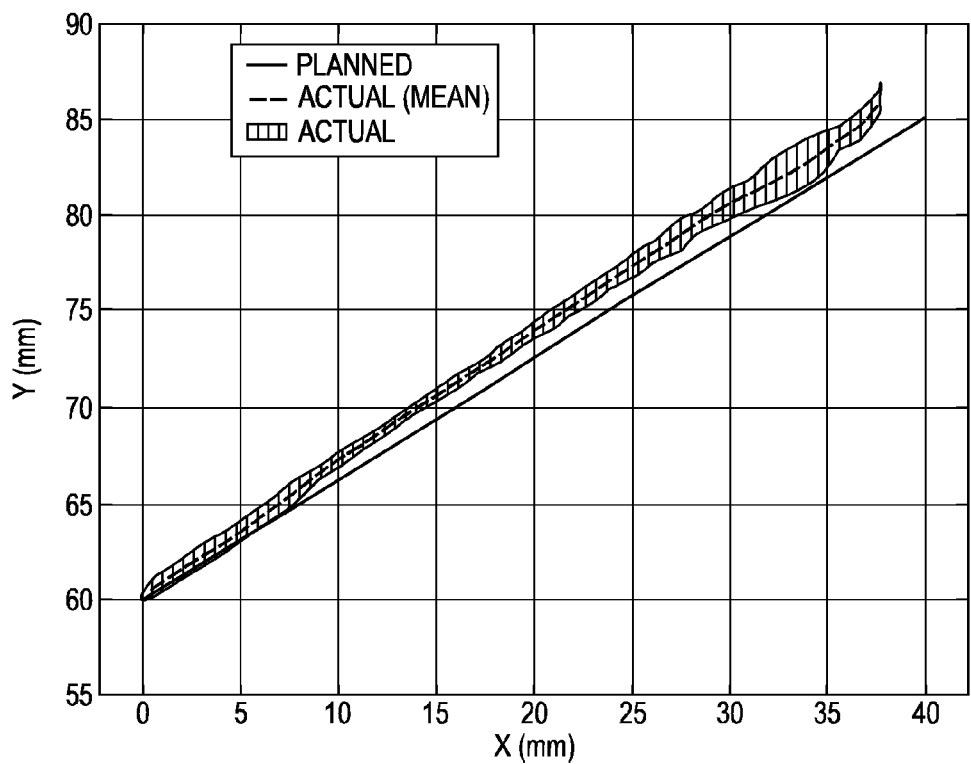
FIG. 15D is a graph of the planned and actual path of a NOTES robotic device traced in a workspace, according to one embodiment.

Using the generated actuator space velocity traces, six open-loop tests were performed. A comparison of the planned path and the actual paths is shown in FIG. 15D. The mean of the actual paths is given as a dotted line with an envelope containing all paths. While the open-loop tests closely follow the desired path, feedback control will improve system performance.

EXAMPLE 2

Figure 16:
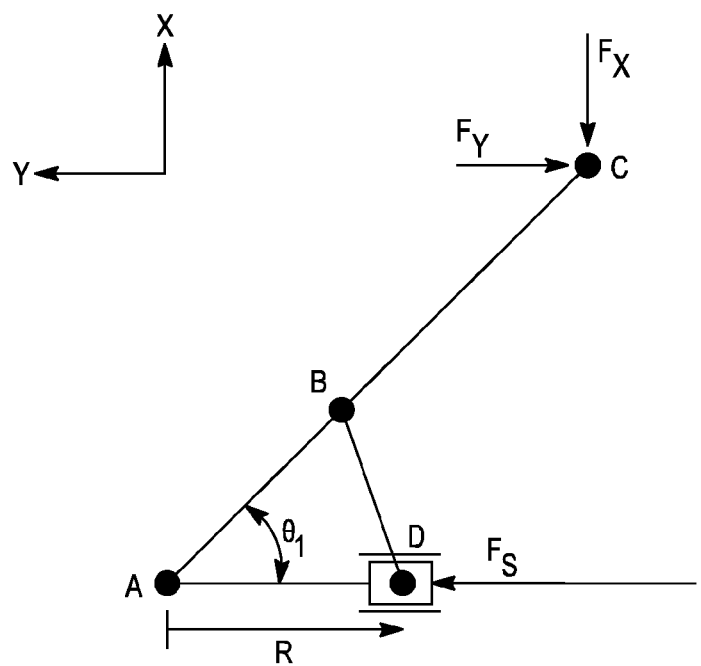
FIG. 16 is a kinematic model of a shoulder joint of a robotic device of the surgical visualization and device manipulation system, according to one embodiment.

The following is an exemplary design of the motion of one embodiment of the shoulder joint of a NOTES robotic device. Here, a departure from typical joint designs was required because of a desire to keep the arm in plane with the body of the robotic device. One example of a kinematic model of the shoulder joint of the NOTES robotic device is shown in FIG. 16. In the present mechanism a powerscrew applies a force ($F_s$) to a slider constrained to move only in the y-direction. The slider mechanism is coupled to the robotic arm (ac) by a link (bd) with rotational degrees of freedom at each end. Length (ab) is constant and defines the length of the arm from the rotation point (a) to the linkage pin (b). Length (ad) represents the distance between the rotation point (a) and the slider (d) Angle $\theta_1$ is the angle between (ab) and (ad). For this particular example, link lengths of the model are shown in Equations 8-11.

$$\overline{ab} = l \quad \text{Equation 8}$$

$$\overline{ac} = a_{3max} \quad \text{Equation 9}$$

$$\overline{ad} = r \quad \text{Equation 10}$$

$$\overline{bd} = d \quad \text{Equation 11}$$

Using these lengths, equations for the amount of force from the slider ($F_s$) that can be translated through the mechanism to the end-effector in the x or y-directions can be derived and are given by Equations 12 and 13 where $F_x$ is the amount of force in the x-direction and $F_y$ is the amount of force in the y-direction.

$$F_x = \frac{2F_s l}{a_{3max}} \tan(\theta_1) \frac{r^2}{(d^2 - l^2) + r^2} \quad \text{Equation 12}$$

$$F_y = \frac{2F_s l}{a_{3max}} \frac{r^2}{(d^2 - l^2) + r^2} \quad \text{Equation 13}$$

In the present kinematic configuration, a very large mechanical advantage is achieved when link bd nears perpendicular to link ad, which is only possible when the ratio of d to l is less than one. Mathematically, at this point the applicable forces (Fx) are infinite. However, when the ratio of d to l is less than one, the range of motion of the shoulder joint becomes limited, with a ratio of d/l of 0.9, yielding a maximum angle of rotation of 65 degrees. In this example, in order to achieve both a large range of motion and the mechanical advantage of the linkage configuration, a d/l ratio of 1 was used. With this ratio, Equations 12 and 13 simplify to Equations 14 and 15 respectively, which were used to determine link length.

$$F_x = \frac{2F_s l}{a_{3max}} \tan(\theta_1) \quad \text{Equation 14}$$

$$F_y = \frac{2F_s l}{a_{3max}} \quad \text{Equation 15}$$

EXAMPLE 3

The following is an exemplary design of the motion of one embodiment of the manipulators of the console. In this example, laparoscopic tool handles are used to control the movement of the NOTES robotic device. Natural and realistic control of the robotic device was achieved by requiring the laparoscopic tool to rotate about the same point as the robotic arm. This point is shown to be physically the same point; however, this point could be a virtual point. Relative motion with respect to the virtual point when the virtual point is not physically in the same location for both the console and the robotic device would create the same effect.

Figure 17:
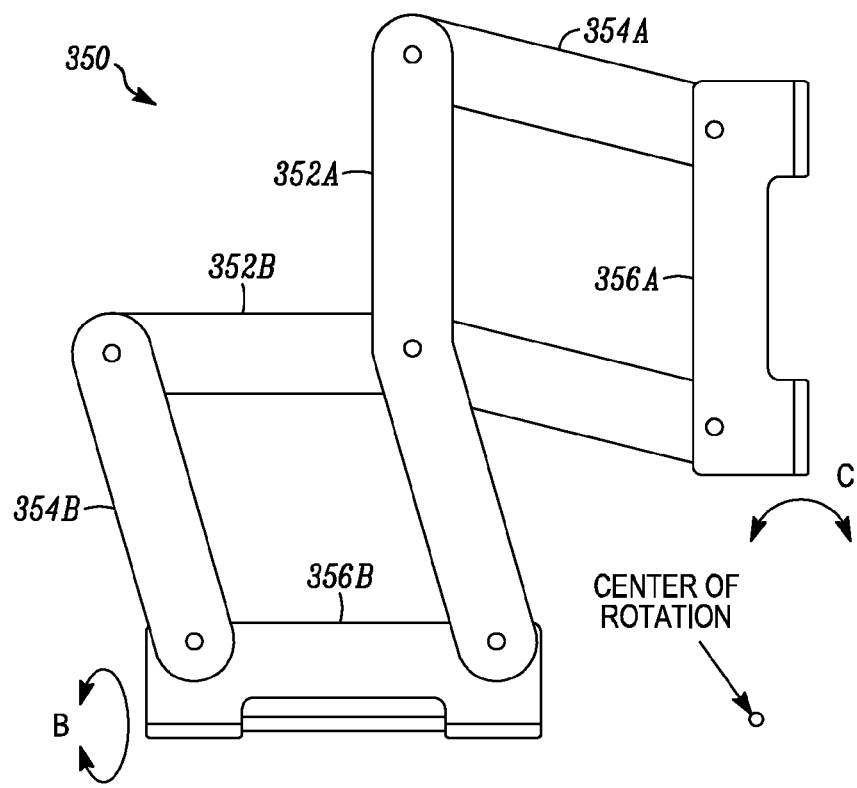
FIG. 17 is a schematic diagram of an offset planar hinge joint of the surgical visualization and device manipulation system, according to one embodiment.
Figure 18A:
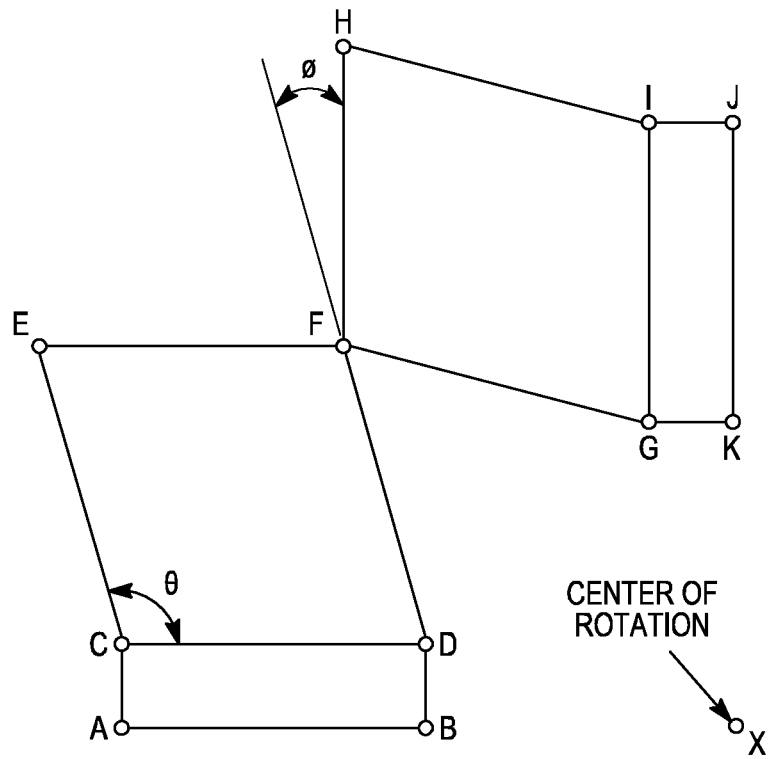
FIG. 18A is a kinematic model of an offset planar hinge joint of the surgical visualization and device manipulation system in a nominal state, according to one embodiment.
Figure 18B:
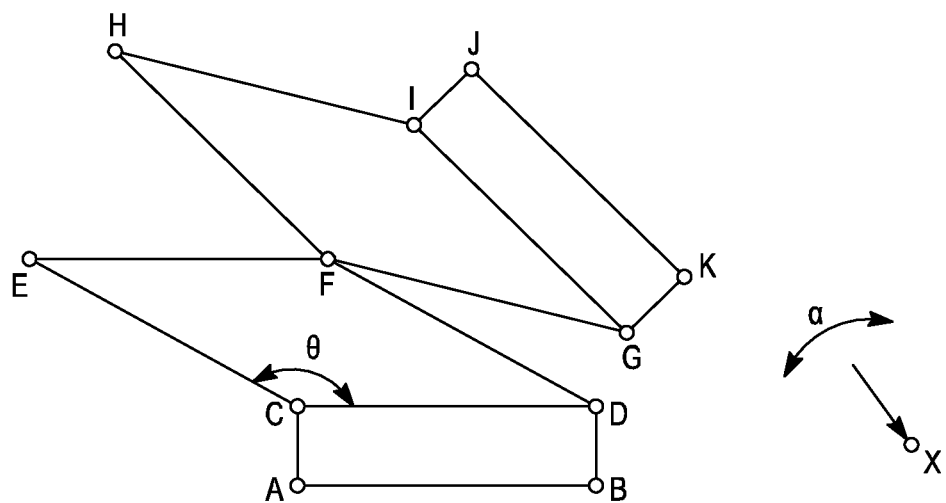
FIG. 18B is a kinematic model of an offset planar hinge joint of the surgical visualization and device manipulation system rotated by an amount alpha, according to the embodiment of FIG. 15A.

In the present example, an "offset planar hinge" similar to that shown in U.S. Pat. No. 5,657,584 was used. The linkage allows the manipulators to rotate about a remote point. An example of an offset planar hinge joint is shown in FIG. 17. The offset planar hinge joint shown in FIG. 17 is similar to offset planar hinge joint shown and described in the discussion of FIGS. 7A and 7B. A kinematic representation of the offset planar hinge joint in the present example is shown in FIGS. 18A and 18B. Equations 16-22 describe the geometry of the linkage. The lengths of the links between pins are listed as the two pin labels (ie. $\overline{ab}$ is the distance between pin a and pin b). Many of the links are of the same length and are grouped as either members of links $L_1$, $L_2$ or $L_3$. The angle $\phi$ is the angle between links $\overline{lh}$ and $\overline{fd}$.

$$\phi = \tan^{-1}\left(\frac{L_3}{L_1}\right) \quad \text{Equation 16}$$

$$\overline{ab} = \overline{cd} = \overline{ef} = \overline{fh} = \overline{gi} = \overline{jk} = L_2 \quad \text{Equation 17}$$

-continued $$\overline{ce} = \overline{df} = \overline{fg} = \overline{hi} = \frac{L_3}{\sin(\phi)} \quad \text{Equation 18}$$

$$\overline{ac} = \overline{bd} = \overline{gk} = \overline{ij} = L_3 \quad \text{Equation 19}$$

$$\vec{ac} \| \vec{cd} \| \vec{ef} \| \vec{ce} \| \vec{df} \quad \text{Equation 20}$$

$$\vec{fh} \| \vec{gi} \| \vec{jk} \quad \text{Equation 21}$$

$$\vec{fg} \| \vec{hi} \quad \text{Equation 22}$$

Equations 20-22 list which links are parallel. With these relationships, the distance from point d to g can be found. This distance is used to determine the maximum rotation of the linkage in the present example. The distance is given in Equation 23 and simplified to Equation 26.

$$\vec{dg} = \frac{L_3}{\sin\phi} \begin{bmatrix} \cos\theta + \cos\phi \\ \sin\theta - \sin\phi \end{bmatrix} \quad \text{Equation 23}$$

$$\sin\phi = \frac{L_3}{\sqrt{L_1^2 + L_3^2}} \quad \text{Equation 24}$$

$$\cos\phi = \frac{L_1}{\sqrt{L_1^2 + L_3^2}} \quad \text{Equation 25}$$

$$\vec{dg} = \sqrt{L_1^2 + L_3^2} \begin{bmatrix} \cos\theta + \frac{L_1}{\sqrt{L_1^2 + L_3^2}} \\ \sin\theta - \frac{L_3}{\sqrt{L_1^2 + L_3^2}} \end{bmatrix} \quad \text{Equation 26}$$

Using the kinematic model, the maximum relative rotation of the leaves in the present example will occur when the distance from point d to g is equal to zero, and a maximum bracket rotation ($\theta_{max}$), for the present example, can be found.

$$|\vec{dg}| = 0 \quad \text{Equation 27}$$

$$\cos\theta_{max} + \frac{L_1}{\sqrt{L_1^2 + L_3^2}} = 0 \quad \text{Equation 28}$$

$$\sin\theta_{max} - \frac{L_3}{\sqrt{L_1^2 + L_3^2}} = 0 \quad \text{Equation 29}$$

$$\tan\theta_{max} = \frac{L_3}{-L_1} \quad \text{Equation 30}$$

$$\theta_{max} = \pi - \phi \quad \text{Equation 31}$$

The relationship between bracket rotation and leaf rotation for the present example is given by Equation 32. Substituting for maximum bracket rotation above will yield maximum leaf rotation, as shown in Equation 33.

$$\alpha = \theta - \phi - \pi \quad \text{Equation 32}$$

$$\alpha_{max} = \frac{\pi}{2} - 2\phi \quad \text{Equation 33}$$

In the present example, the design and positioning of the offset planar hinge joints are based on several factors. In order to keep the offset planar hinge joints reasonably sized, the offset angle of the base leaf was set on the order of 30°. In this example, the maximum rotation of the manipulators is limited by the offset angle, however designing for larger maximum leaf rotation will allow for sufficient rotation of the manipulators. Measurement of the position of the manipulators allows for use as controllers for the robotic device. As previously shown, rotation of the manipulators is directly related to bracket rotation (Equation 32). In the present example, this rotation can be measured using potentiometers. Further, rotation of the offset planar hinge joints about the connecting pin to the console is also done using potentiometers. These two measurements allow for the position of the manipulators to be determined. Translation of each of the manipulators about its axis can be determined using mechanical switches or linear potentiometers. Furthermore, the squeezing and releasing of the handles of the manipulators is monitored. Those skilled in the art will recognize and understand that various sensors are available in the art for monitoring and measuring rotation, translation, pressure, and force.

The surgical visualization and device manipulation system generally includes a console having a visual display and a set of manipulators, a robotic device positioned within a body cavity and a connection component operably connecting the console and the robotic device. The system provides a "virtual hole" effect by displaying images captured by the robotic device on the visual display. The console may be positioned directly over the body cavity such that as the images of the body cavity are being fed to the visual display, the surgeon feels as if he is looking directly into the body cavity of the patient. The surgeon can then operate and control the manipulators as if the manipulators were connected to the robotic device positioned within the body cavity at the surgical site. In addition to providing a "virtual hole" effect, the system also allows a surgeon to perform a procedure on a patient located at another location. As the surgeon views visual display and operates manipulators, the robotic device responds to the movements of the manipulators and performs the movements dictated by the surgeon through the manipulators.

Although the surgical visualization and device manipulation system has been described with reference to preferred embodiments, persons skilled in the art will recognize that changes may be made in form and detail without departing from the spirit and scope of the invention.

What is claimed is:
1. A surgical system comprising:
   (a) a console positioned outside a patient's body comprising a visual display and at least one manipulator arm;
   (b) a robotic device comprising:
      (i) a device body;
      (ii) a camera configured to transmit visual images to the visual display;
      (iii) a first robotic arm comprising a first end effector, wherein the first robotic arm is coupled to a first end of the device body;
      (iv) a second robotic arm comprising a second end effector,
         wherein the second robotic arm is coupled to a second end of the device body, wherein the robotic device is sized to be inserted through a standard laparoscopic port and configured to be positioned completely within a body cavity of a patient, and
wherein the first and second robotic arms are configured such that the first and second robotic arms are not positionable in any enclosure of the robotic device; and
(c) a connection component operably coupling the console and the robotic device,
wherein the console is further configured to be positioned in direct physical contact with the patient's body during use.

2. The system of claim 1, wherein the console further comprises a console magnet and the robotic device further comprises a device magnet capable of magnetic communication with the console magnet.

3. The system of claim 1, wherein the manipulator arm is operably coupled to the robotic device via the connection component.

4. The system of claim 1, wherein the connection component is a wireless connection component.

5. The system of claim 1, wherein the manipulator arm is positioned relative to the visual display so as to appear to be penetrating the visual display.

6. The system of claim 1, further comprising a stabilization component coupled to the console.

7. A surgical system comprising:
(a) a robotic device sized to be inserted through a standard laparoscopic port, the device comprising:
(i) a device body;
(ii) first and second robotic arms operably coupled with the device body, wherein each of the first and second robotic arms comprises an end effector, wherein the first robotic arm is coupled to a first end of the device body and the second robotic arm is coupled to a second end of the device body, and wherein the first and second robotic arms are configured such that the first and second robotic arms are not positionable in any enclosure of the robotic device; and
(iii) a camera associated with the device body;
(b) a console positioned outside a patient's body, wherein the console is configured to be positioned in direct physical contact with the patient's body during use, the console comprising:
(i) at least one manipulator arm operably coupled with the console, wherein the at least one manipulator arm is configured to be in communication with at least one of the first and second robotic arms; and
(ii) a visual display disposed on the console, the visual display configured to receive images from the camera; and
(c) a connection component operably coupling the console and the robotic device.

8. The system of claim 7, wherein the console further comprises a console magnet and the robotic device further comprises a device magnet capable of magnetic communication with the console magnet.

9. The system of claim 7, wherein the at least one manipulator arm is operably coupled to the robotic device via the connection component.

10. The system of claim 7, wherein the at least one manipulator arm is positioned relative to the visual display so as to appear to be penetrating the visual display.

11. A surgical system comprising:
(a) a robotic device sized to be inserted through a standard laparoscopic port, the device comprising:
(i) an elongate device body configured to be positioned within a cavity of a patient;
(ii) a first robotic arm operably coupled with a first end of the device body, the first robotic arm comprising a first end effector;
(iii) a second robotic arm operably coupled with a second end of the device body, the second robotic arm comprising a second end effector; and
(iv) a camera associated with the device body, wherein the first and second robotic arms are configured such that the first and second robotic arms are not positionable in any enclosure of the robotic device;
(b) a console positioned outside the patient's body, the console comprising:
(i) first and second manipulator arms operably coupled with the console, wherein the first and second manipulator arms are configured to be in communication with the first and second robotic arms; and
(ii) a visual display disposed on the console, the visual display configured to receive images from the camera; and
(c) a connection component operably coupling the console and the robotic device.

12. The system of claim 11, wherein the robotic device is configured such that it is not constrained by any entry incision.

13. The system of claim 11, wherein the console is configured to be positioned in contact with the patient's body during use.

14. The system of claim 11, wherein the console is configured to be disposed at a location remote from the patient.

15. The system of claim 11, wherein the console further comprises a console magnet and the robotic device further comprises a device magnet capable of magnetic communication with the console magnet.

16. A surgical system comprising:
(a) a robotic device sized to be inserted through a standard laparoscopic port and configured to be positioned in a body cavity of a patient, wherein the robotic device comprises:
(i) a device body;
(ii) a first robotic arm operably coupled with a first end of the device body, the first robotic arm comprising a first end effector;
(iii) a second robotic arm operably coupled with a second end of the device body, the second robotic arm comprising a second end effector; and
(iv) a camera associated with the device body, wherein the camera is positioned between the first and second robotic arms,
wherein the first and second robotic arms are configured such that the first and second robotic arms cannot be positioned into any enclosure of the robotic device;
(b) a console positioned outside the patient's body, the console comprising:
(i) first and second manipulator arms operably coupled with the console, wherein the first and second manipulator arms are configured to be in communication with the first and second robotic arms; and
(ii) a visual display disposed on the console, the visual display configured to receive images from the camera; and
(c) a connection component operably coupling the console and the robotic device.

17. The system of claim 16, wherein the console is configured to be disposed at a location remote from the patient.

18. The system of claim 16, wherein the first and second manipulator arms are operably coupled to the robotic device via the connection component.

19. The system of claim 16, wherein the connection component is a wired connection component.

20. The system of claim 16, wherein the manipulator arm is positioned relative to the visual display so as to appear to be penetrating the visual display.

* * * * *